United States Patent [19]

Strosser

[11] Patent Number: 4,624,180
[45] Date of Patent: Nov. 25, 1986

[54] ELECTRONIC BALE DENSITY CONTROLLER

[75] Inventor: Richard P. Strosser, Akron, Pa.

[73] Assignee: New Holland, Inc., New Holland, Pa.

[21] Appl. No.: 773,472

[22] Filed: Sep. 6, 1985

[51] Int. Cl.$^4$ .................................................. B30B 15/26
[52] U.S. Cl. ........................................ 100/41; 100/43; 100/191
[58] Field of Search ............... 100/35, 41, 43, 191, 100/192, 189; 56/341

[56] References Cited

U.S. PATENT DOCUMENTS

| | | | |
|---|---|---|---|
| 4,037,528 | 7/1977 | White | 100/191 |
| 4,118,918 | 10/1978 | White | 56/341 |
| 4,125,071 | 11/1978 | Young | 100/191 |
| 4,132,163 | 1/1979 | White | 100/42 |
| 4,168,659 | 9/1979 | Yatcilla et al. | 100/43 |
| 4,184,312 | 1/1980 | Oosterling et al. | 56/341 |
| 4,275,550 | 6/1981 | Swenson et al. | 56/341 |
| 4,280,403 | 7/1981 | Alderson | 100/43 |
| 4,489,648 | 12/1984 | Naaktgeboren | 100/191 |
| 4,514,968 | 5/1985 | Underhill | 56/341 |
| 4,525,991 | 7/1985 | Naaktgeboren | 56/341 |

*Primary Examiner*—Billy J. Wilhite
*Attorney, Agent, or Firm*—Griffin, Branigan, & Butler

[57] ABSTRACT

An agricultural baling machine controls the density of bales of crop material discharged therefrom by monitoring the stress experienced by a reciprocably driven plunger assembly (22) employed to apply a compactive force to crop material introduced into a bale case (20). The bale case (20) is comprised of rails (54, 56) which are positionably adjustable in response to applied tension in a manner whereby the dimensions of the bale case (20) are changeable, thereby facilitating a change in the degree of resistance caused by the bale case (20) to crop material movement therein. Signals produced by stress sensors (124, 126, 128, 130) mounted relative to the plunger assembly (22) are analyzed by a programmed signal processor (200) which accordingly generates a control signal for controlling a servo valve (61). In response to the control signal the servo valve (61) governs the degree of tension applied to the bale case raisl (54, 56) and thereby adjusts the degree of resistance to crop movement in the bale case (20). The analysis performed by the signal processor (200) results in the generation of a pulse width modulated control signal that enables the servo valve (61) to adjust the degree of resistance to crop movement in the bale case (20) so that the stress experienced by the plunger assembly (22) is maintained near a predetermined level in accordance with desired bale density.

29 Claims, 25 Drawing Figures

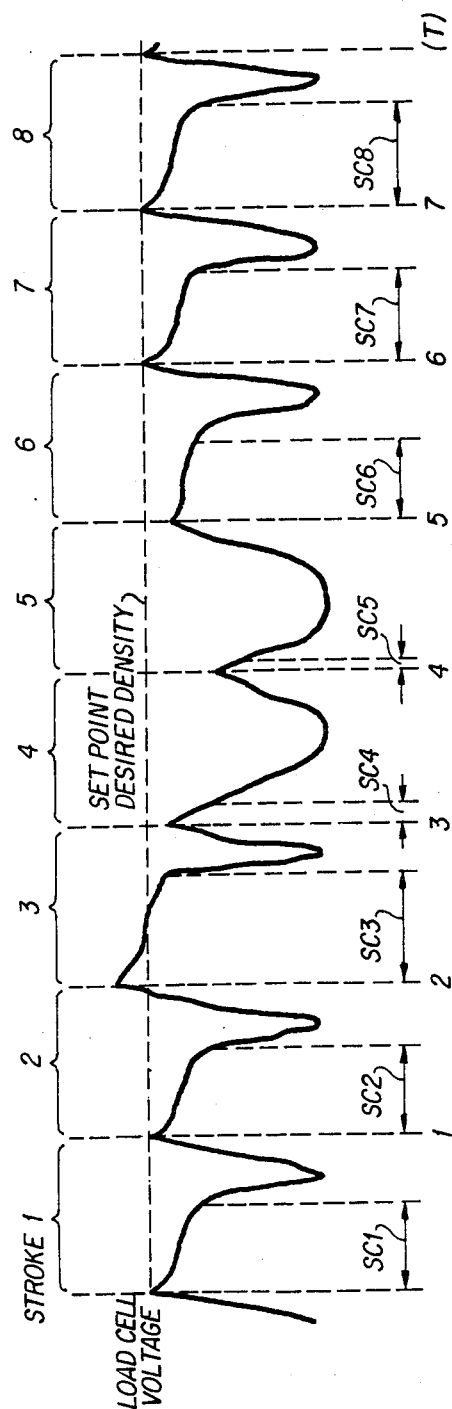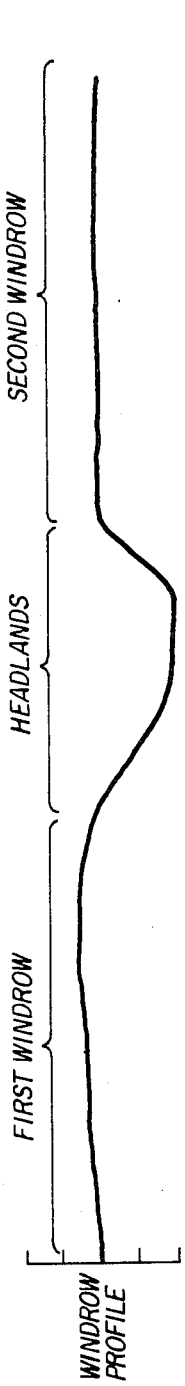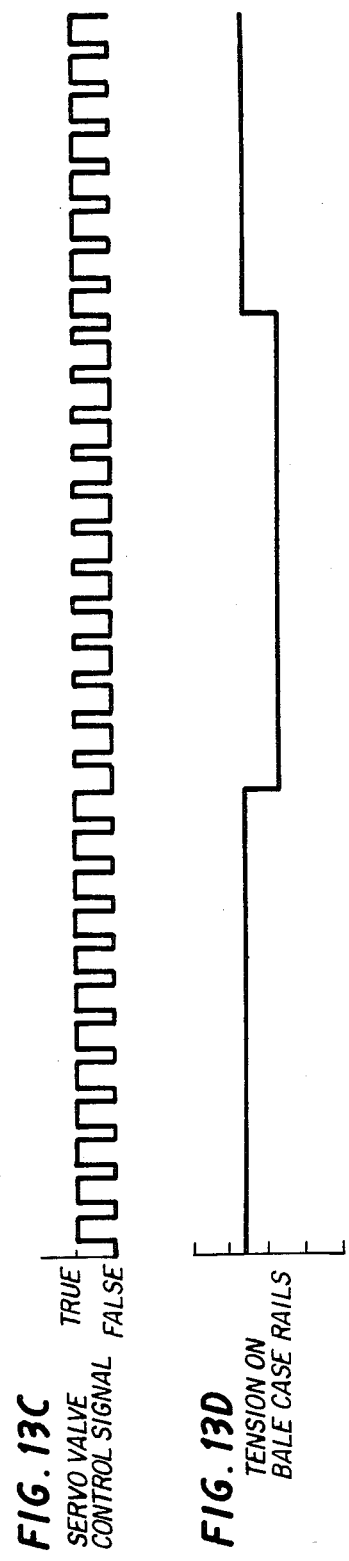

ELECTRONIC BALE DENSITY CONTROLLER

BACKGROUND

I. Field of The Invention

The present invention relates generally to agricultural balers and, in particular, to density control methods and apparatus for such balers.

II. Prior Art and Other Considerations

Agricultural balers have a bale case into which crop or silage material is introduced. The bale case, generally of a rectangular shape, is defined by rails which determine the height and width of the bale case. A plunger is reciprocably disposed in a forward portion of the bale case to form crop material into rectangular bales. These rectangular bales are pushed through a rearward portion of the bale case where they are bound in a conventional manner with suitable material such as twine before being discharged from the baler.

In the baler art it is known that bale density may be controlled by changing the position of one or more of the rails defining the bale case. Numerous types of mechanisms have been provided for performing this function such as those shown in U.S. Pat. Nos. 4,125,071; 4,037,528; and 4,489,648. In various ones of these known mechanisms tensioning systems comprising hydraulic cylinders are actuated to change the position of the bale case rails.

Various prior art methods exist for controlling the actuation of the hydraulic cylinders and for thereby changing the position of the bale case rails in order to control the density of the material being baled therein. U.S. patent application Ser. No. 773,471, entitled "Bale Density Control Sensing Apparatus and Method" simultaneously filed herewith by Cecil R. Sudbrack et al. and incorporated herein by reference, discloses new method and apparatus wherein sensor means are provided for monitoring the compression load on each of two connecting rods which connect a plunger element to plunger driving means. Sensors such as strain gauge sensors are used for electronic decisions regarding adjustments of the hydraulic cylinders necessary for controlling bale density. The electronic decisions are based on the compression load required to push the material being baled through the tensioned bale case. The required compression load is dependent upon factors such as the degree of frictional drag between the bale case and the material being baled. By using the sensors to monitor the compression load and by actuating the hydraulic cylinders comprising the bale case tensioning system to maintain a constant compression load, a constant bale density results with respect to each charge of material introduced into the bale case.

The amount of crop material being introduced into a bale case can fluctuate greatly as the tractor-pulled baler travels over a windrowed field. Fluctuations in crop flow into the bale case can present problems when the compression load is being continually monitored for the purpose of adjusting the bale case tensioning system. For example, when a baler enters the headlands, crop material ceases to enter the bale case. When the baler is in the headlands the compression load on the connecting rods significantly decreases. If the tension rail pressure were to be increased to tighten the bale case in accordance with the decreased compression load, the baler would enter the next windrow with a highly tensioned rail pressure. Ingestion of a considerable amount of new crop material into a highly tensioned bale case can overload the connecting rods which are used to drive the plunger.

In view of the foregoing, it is an object of the present invention to provide bale density control method and apparatus which takes into consideration fluctuations in the amount of crop flow into the bale case.

An advantage of the present invention is the provision of method and apparatus wherein crop ingestion measurements are made by the same sensors used for bale density control.

Another advantge of the present invention is the provision of method and apparatus wherein crop ingestion measurements take into consideration power take off (PTO) speed.

Yet another advantage of the present invention is the provision of method and apparatus wherein PTO speed is determined from information available from bale density control sensors, thus avoiding the employment of a separate PTO sensor and the external wiring associated therewith.

SUMMARY

An agricultural baling machine controls the density of bales of crop material discharged therefrom by monitoring the stress experienced by a reciprocably driven plunger assembly employed to apply a compactive force to crop material introduced into a bale case. The bale case is comprised of rails which are positionably adjustable in response to applied tension in a manner whereby the dimensions of the bale case are changeable, thereby facilitating a change in the degree of resistance caused by the bale case to crop material movement therein. Signals produced by stress sensors mounted relative to the plunger assembly are analyzed by a programmed signal processor which accordingly generates a control signal for controlling a servo valve. In response to the control signal the servo valve governs the degree of tension applied to the bale case rails and thereby adjusts the degree of resistance to crop movement in the bale case. The analysis performed by the signal processor results in the generation of a pulse width modulated control signal that enables the servo valve to adjust the degree of resistance to crop movement in the bale case so that the stress experienced by the plunger assembly is maintained near a predetermined level in accordance with desired bale density.

Lest the bale case rail tension be too quickly adjusted during a period of insufficient crop material ingestation, the signal processor also monitors the quantity of crop material ingestation and precludes the increasing of tension application to the bale case rails unless a predetermined minimum level of crop ingestation is being achieved. In this regard, the signal processor analyzes the signals from the stress sensors as a waveform and obtains therefrom an indication of the degree of bale slippage through the bale case, the degree of bale slippage being related to the quantity of crop ingestation. Using the waveform the signal processor also normalizes the indication of quantity ingestation with respect to a reference PTO speed.

In one embodiment the stress sensors comprise two load cells of shear stress strain gages, each load cell including four such strain gages. One load cell is mounted on a left wrist pin of the plunger assembly while the other load cell is mounted on a right wrist pin of the plunger assembly. The plunger assembly further comprises a plunger element which is connected through the left and right wrist pins and left and right connecting rods (also known as conrods) to appropriate reciprocating driving apparatus. Being mounted on the wrist pins, the load cells sense the stress experienced by the left and right connecting rods and produce AC signals indicative of the magnitude of the sensed stress.

The signal processor is programmed with routines of coded instructions whereby the signal processor receives the AC signals produced by the left and right load cell; processes and analyzes values corresponding to the load cell signals; and, generates a pulse width modulated control signal for application to the servo valve (which governs the tension applied to the bale case rails). In addition, the signal processor is programmed with routines of coded instructions which facilitate input and output operations with an operator, including output display operations.

The signals produced by the left and right load cells interrupt processing by the signal processor and prompt the execution of a routine IRQT. In this regard, sensor interrupts are grouped in sets of four with the interrupts in each set being in a predetermined order.

In a given set of sensor interrupts, a first interrupt corresponds to a positive phase signal from the right load cell; the second interrupt corresponds to a negative phase signal from the right load cell; the third interrupt corresponds to a positive phase signal from the left load cell; and, the fourth interrupt corresponds to a negative phase signal from the left load cell. When the signal processor has received digitally converted sensor output signals (expressed in terms of voltage) for both positive and negative phases of a given load cell, the signal processor determines the difference between the positive and negative phase signal magnitudes and uses the same as an indication of the stress currently experienced by that load cell.

After the signal processor obtains a value indicative of the magnitude of stress currently experienced by a load cell, the signal processor stores the current stress magnitude value in a moving average buffer wherein a plurality of previous stress magnitudes as sensed by the same load cell are also stored. The values stored in the moving average buffer are interpreted by the signal processor as representing at least a portion of a waveform. The values in the moving average buffer are averaged and the current average value is henceforth used as an indication of the current magnitude of the output voltage signal produced by the load cell. During on-going processing the signal processor knows by checking a flag THRESHOLD whether a rising portion or a falling portion of the waveform is currently being analyzed.

In analyzing a waveform from a given load cell, the signal processor determines sensor voltage peaks for the given load cell and, so long as the sensed voltage signal is within a predetermined neighborhood of the sensor voltage peak, updates a counter used for indicating both the degree of bale slippage through the bale case and the quantity of crop material ingested into the bale case. In this regard, in observing sensor output voltage signal waveforms it has been noted that, following a voltage peak, a voltage plateau is formed before the voltage tapers off significantly, and that the duration of this plateau corresponds substantially to the degree of bale slippage which occurs in the bale case following the application of compactive force by the plunger. Further, the degree of bale slippage has been observed as corresponding to the quantity of crop material being introduced into the bale case from the particular windrow over which the baler is travelling. Thus, voltage peak values and slip count values for each plunger stroke are maintained for each load cell, i.e. for both the left load cell and the right load cell.

The signal processor analyzes the right load cell waveforms and the left load cell waveforms in alternating fashion in accordance with the aforedescribed set of sensor interrupts. If, after a complete set of sensor interrupts has been received and ensuing waveform analyzed, a vicinity of a new voltage peak is determined, the signal processor executes a routine LOOP.

In routine LOOP the left and right load cell voltage values are summed to obtain a total conrod load value. The total conrod load value is compared to a user-input set point value which is indicative of the desired density of the bales to be discharged from the baler. The difference between the user-input set point value and the total conrod load value is stored at location DENSITY ERROR and, after adjustment and normalization, is eventually used as a feedback correction factor for modulating the pulse width of the control signal applied to the bale case tension-affecting servo valve.

Before using the value DENSITY ERROR for modulating the pulse width of the servo valve contol signal, routine LOOP preforms two precautionary checks: (1) checking whether the PTO RPM is below a predetermined RPM value, and (2) checking whether an sufficient quantity of crop material is being introduced into the bale case. If the result of either check is affirmative, routine LOOP serves to clamp the tension applied to the bale case rails at a previous degree of tension by keeping the pulse width of the servo valve control signal modulated in its previous manner.

In the above regard, in determining whether a sufficient quantity of crop material is being introduced into the bale case, and in accordance with the bale slip observations noted above, the routine LOOP uses the count maintained in the left slip counter or the right slip counter (whichever is greater) and then normalizes the greater bale slip counter value with respect to the maximum PTO RPM. If the normalized greater slip counter value is less than a minimum threshold value, routine LOOP realizes that an insufficient quantity of crop material is being ingested.

If neither of the precautionary checks undertaken by routine LOOP has affirmative results, routine LOOP uses the value in location DENSITY ERROR to obtain a new pulse width modulation (PWM) value. Routine LOOP checks to determine whether the new pulse width modulation value is within acceptable magnitude limits; linearizes the new pulse width modulation value using a look-up table; and, compensates the linearized new pulse width modulation value to take into consideration supply voltage variations to the servo valve. Routine LOOP then calculates a TIME ON value and a TIME OFF value for use by a timer comprising the signal processor in the generation of the servo valve control signal.

In addition to the sensor interrupts described above, the signal processor also periodically receives a non-maskable interrupt which prompts the signal processor to execute a routine NMIR. Execution of routine NMIR results in the generation of the pulse width modulated signal which controls the bale case tension-affecting servo valve. The pulse width modulated signal is TRUE for a period of time related to the value TIME ON and is FALSE for a period of time related to the value TIME OFF. The duration of the TRUE signal is indicative of the degree of bale case tension to be applied via the servo valve. As seen from the foregoing, the change in the magnitude of the "on" time pulse, and hence the change in bale case tension, is related to the density error value as sensed by the load cells.

In addition to the foregoing, the signal processor executes a routine BLSH. Routine BLSH determines which of the left or right load cells is experiencing the greater stress and provides both an indication of the degree of the stress differential and an indication of the direction in which the baler should be manuevered in order to rectify the stress differential.

BRIEF DESCRIPTION OF THE DRAWINGS

The foregoing and other objects, features, and advantages of the invention will be apparent from the following more particular description of preferred embodiments as illustrated in the accompanying drawings in which reference characters refer to the same parts throughout the various views. The drawings are not necessarily to scale, emphasis instead being placed upon illustrating the principles of the invention.

FIG. 13A is a graph showing the magnitude of the sensed stress experienced by conrods of a baling apparatus according to an embodiment of the invention over a time span of eight strokes;

FIG. 13B is a graph showing the profile of a hypothetical windrow over the time span of FIG. 13A;

FIG. 13C is a graph showing the value of a control signal applied to a servo valve over the time span of FIG. 13A; and, FIG. 13D is a graph showing the magnitude of the tension on bale case rails as a result of the application of the control signal of FIG. 13C.

DETAILED DESCRIPTION OF THE DRAWINGS

Figure 1:
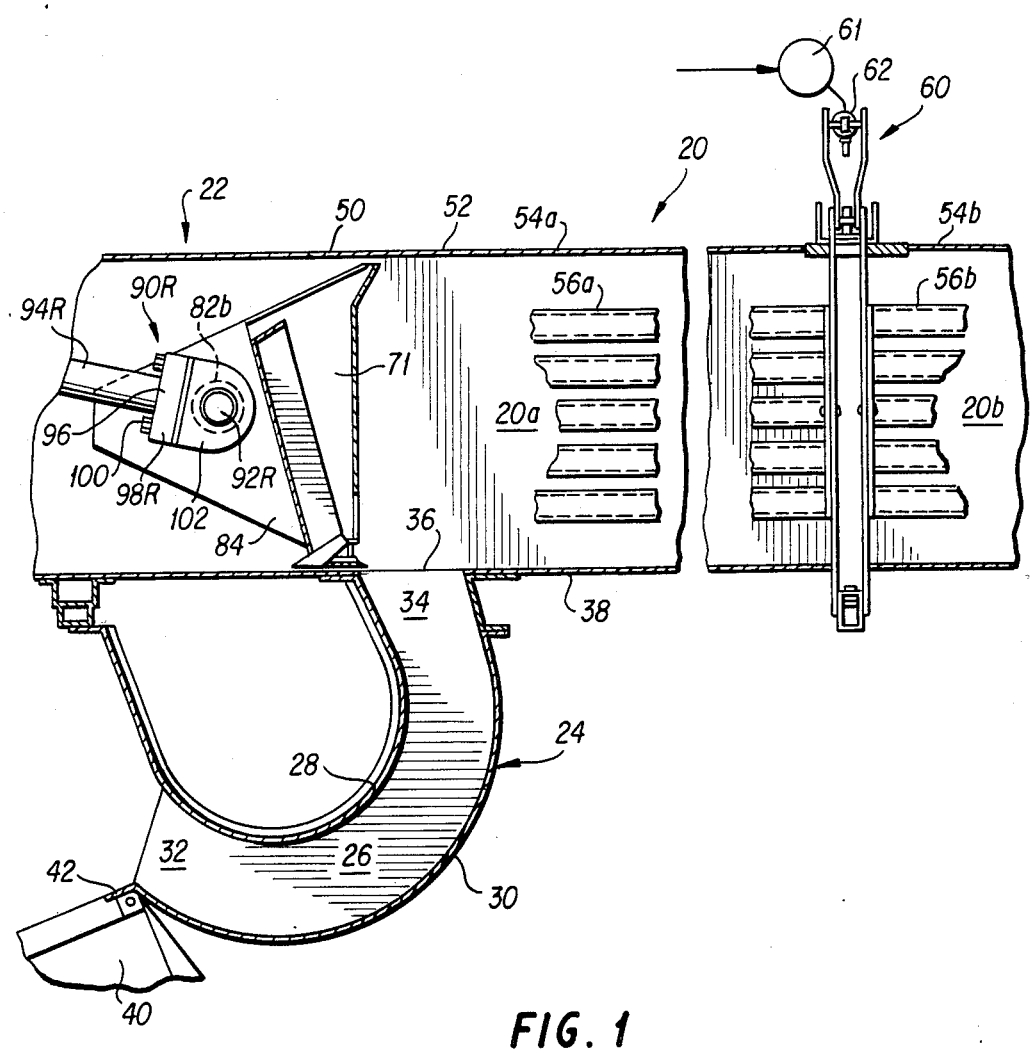
FIG. 1 is a partially sectioned side view of a portion of an agricultural baling apparatus according to an embodiment of the invention which shows a portion of a bale case with a plunger disposed at a forward end thereof.

FIG. 1 shows a portion of an agricultural baling machine which comprises a bale case 20, a portion of which is shown in FIG. 1. Although not shown herein, it is understood that the bale case 20 is mounted on a frame which is supported by wheels. A tongue extends forwardly from the bale case 20 for attachment to a tractor (also not shown). A plunger assembly 22 is reciprocably disposed in the bale case 20 to form crop material into rectangular bales.

A feed chamber 24 is mounted underneath the bale case 20 and includes a curved duct 26 having top and bottom walls 28 and 30, respectively, and sidewalls. The curved duct 26 is open at its lower end 32 and communicates at its upper end 34 with an inlet opening 36 formed in a bottom wall 38 of the bale case 20. A pickup device 40 of a conventional type is partially shown in FIG. 1 as being pivotally connected at 42 to the feed chamber 24. The pickup device 40 includes a plurality of fingers which are rotatable for lifting crop material from the ground and delivering it toward the feed chamber 24. The details of one suitable type of feed chamber and feed mechanisms provided therein are understood from U.S. Pat. No. 4,525,991 to Naaktgeboren which is incorporated herein by reference.

The bale case 20 has a forward portion 50 (in which the plunger assembly 22 is reciprocably disposed) and a rearward portion 52 (in which are provided bale case areas 20a and 20b). The bale case 20 is comprised of a top rail (including top rail sections 54a and 54b); siderails (including siderail sections 56a and 56b); and, a bottom rail or bottom wall 38.

A tension adjusting system 60 is provided for changing the position of the first and second sections 54a, 54b of the top rail and for changing the positions of the first and second sections 56a, 56b of the siderails to adjust the dimensions of the chamber areas 20a and 20b of the bale case rearward portion 52 to thereby adjust bale density. The tension adjusting system 60 comprises a servo valve 61; a hydraulic cylinder unit 62; and mechanical tensioning elements. In the illustrated embodiment the servo valve 61 is a current-controlled pressure valve such as the type marketed by FEMA Corporation as model PPC84600CF.

The tension adjusting system 60 is utilized to govern the degree of resistance provided by the bale case 20 to movement of crop material therein in order to adjust bale density, which may have the effect of changing the height and width of the bale case chamber areas 20a and 20b in appropriate circumstances. For example, by contracting the hydraulic cylinder unit 62, the bale case chamber areas 20a and 20b can, in appropriate circumstances, be reduced in height and width, thereby usually resulting in higher bale density. Conversely, by extending the hydraulic cylinder unit 62, the bale case chamber areas 20a and 20b can, in appropriate circumstances, be enlarged in height and width, thereby usually resulting in lower bale density. The details of one suitable type of mechanical tension elements comprising the tension adjusting system 60 are understood from U.S. Pat. No. 4,489,648 to Naaktgboren which is incorporated herein by reference, it being understood that other suitable types of mechanical tensioning elements can also be used.

Figure 2:
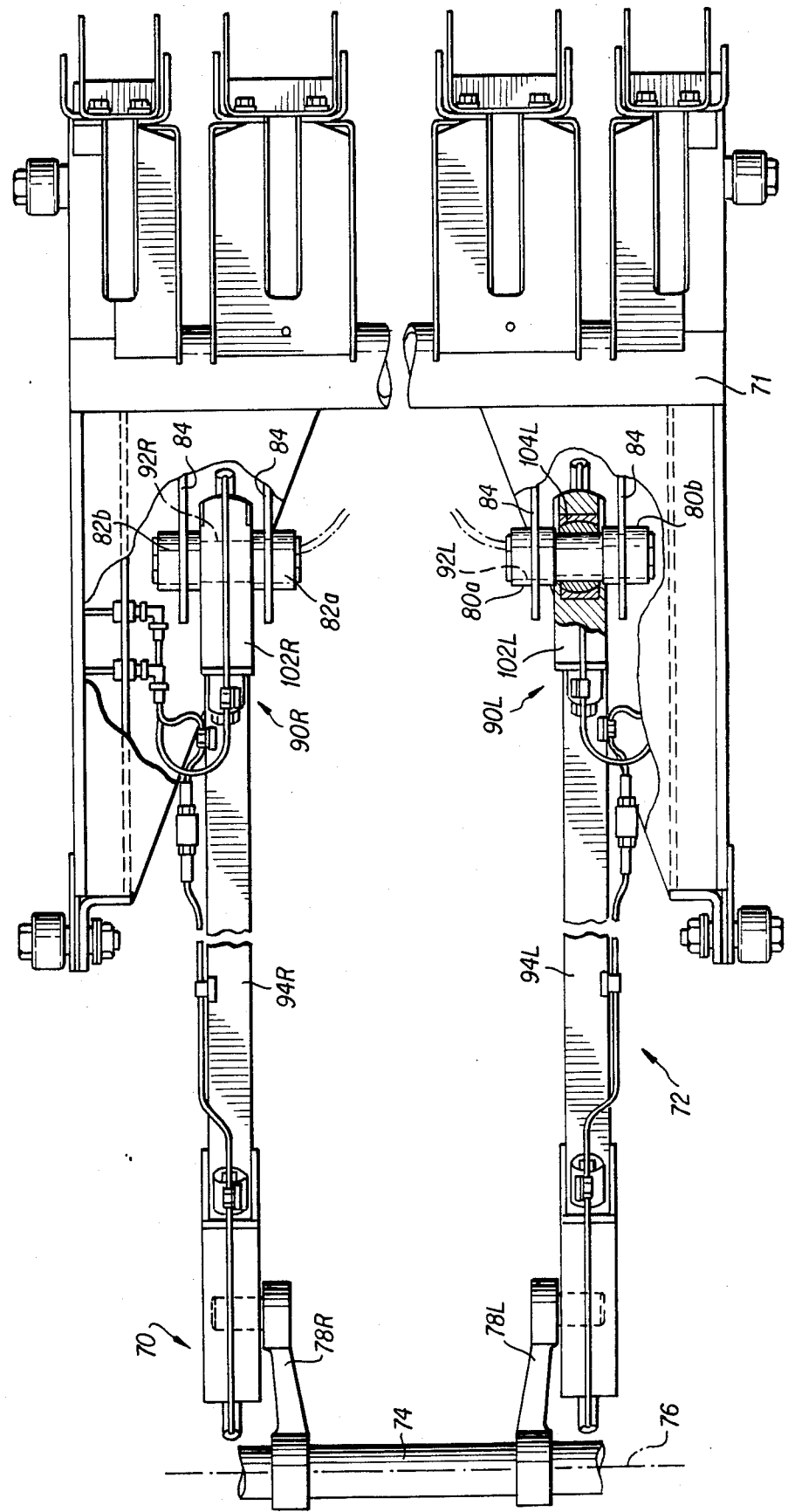
FIG. 2 is a top view, partially sectioned, of a portion of a bale case plunger assembly and portions of associated plunger driving means according to an embodiment of the invention.

FIG. 2 shows elements included in the forward portion of the bale case 50, including a portion of the plunger assembly 22 and plunger driving means 70. As used herein the plunger assembly includes a plunger element 71 and connecting means 72 for connecting the plunger element 71 to the plunger driving means 70.

The plunger driving means 70 comprises a crankshaft 74 (having a major axis 76) and left and right cranks 78L, 78R, respectively, connected to crankshaft 74 to be driven in phase with one another. Although not shown herein, it is understood that the crankshaft 74 is ultimately connected through a chain drive to a reduction gear box. Power from the PTO is transmitted through gearing in the reduction gear box and the chain drive to the crankshaft 74.

The plunger element 71 has two pairs of hubs mounted on a forward side thereof (that is, the side of the plunger element which does not contact the crop material). In this regard, a left hub pair 80a, 80b is provided on the left side of the plunger element 71 and a right hub pair 82a, 82b is provided on the right side of the plunger element 71. Each hub is essentially a hollow cylinder mounted inter alia by member 84 on the forward side of the plunger element 71.

The connecting means 72 comprises left and right connecting rod assemblies (also known as conrods) 90L, 90R, respectively, and left and right wrist pins 92L, 92R, respectively. Each connecting rod assembly 90 has a first end connected to the plunger drive means 70 and a second end connected to its respective wrist pin 92. In this respect, the first end of each connecting rod assembly 90 is connected to its respective crank 78 by a suitable bearing (not shown). The second end at each connecting rod assembly 90 comprises a weld assembly at which an elongated connecting rod 94 is welded (at 96) to a plate 98. Plate 98 is secured by fasteners 100 to a bearing housing 102. The bearing housing 102 has a bearing 104 therein adapted to centrally receive an intermediate portion of the respective wrist pin 92.

Figure 3A:
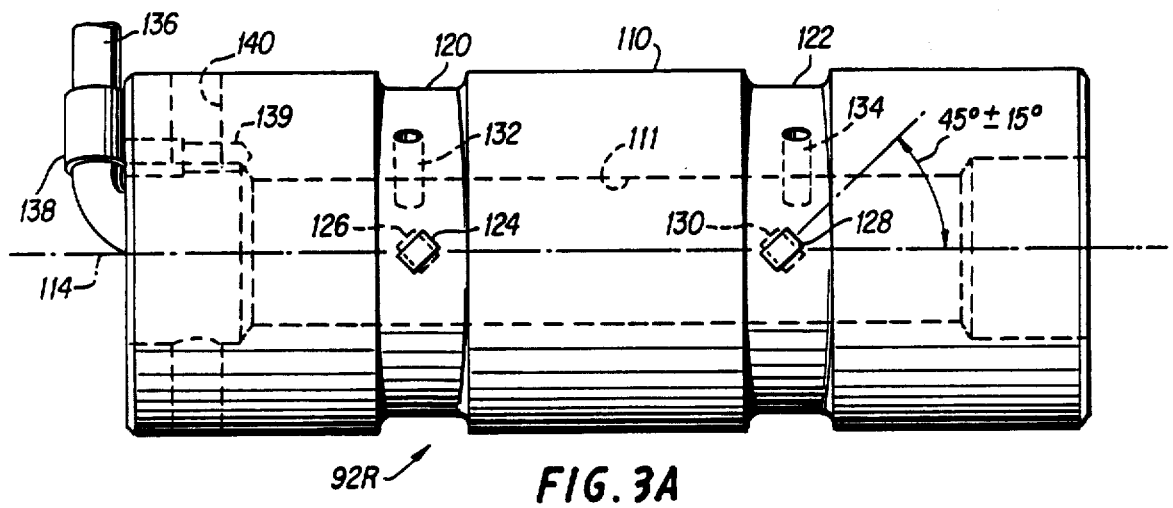
FIG. 3A is a top view of a wrist pin according to an embodiment of the invention wherein shear stress sensors are mounted on an exterior surface of the wrist pin.
Figure 3B:
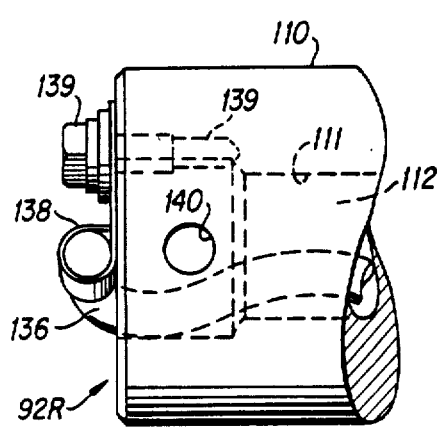
FIG. 3B is a front view of a portion of the wrist pin of FIG. 3A.
Figure 3C:
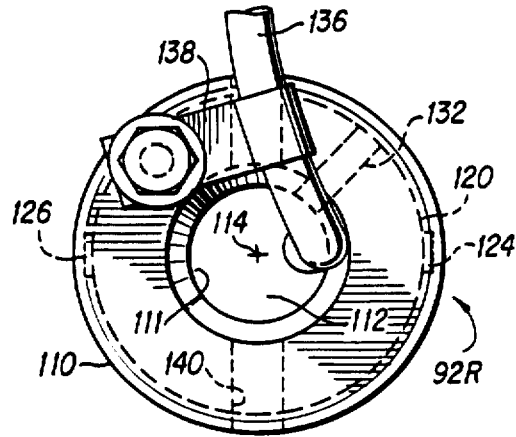
FIG. 3C is an end view of the wrist pin of FIG. 3A.

FIGS. 3A, 3B, and 3C show an embodiment of a wrist pin 92 having sensors mounted thereon in two shear planes. Wrist pin 92 is essentially a hollow cylinder with an exterior cylindrical surface 110 and an interior cylindrical surface 111 which defines a hollow, essentially cylindrical cavity 112. The wrist pin 92 has a major axis 114 as shown in FIG. 3A.

Shear stress sensor means is mounted on each wrist pin 92. Two essentially annular recesses or channels 120 and 122 are formed on the exterior surface 110 of each wrist pin 92. In each annular recess 120, 122 two shear stress sensors such as strain gages are mounted essentially 180 degrees apart about the major axis 114. In this respect, in annular recess 120 a strain gage 124 is mounted on the front of wrist pin 92 and strain gage 126 on the back of wrist pin 92. Strain gages 128 and 130 are mounted in similar manner in annular recess 122. The strain gages 124, 126, 128, and 130 function together and are hereinafter referred to collectively as a load cell 131. Thus, a left load cell 131L is provided on wrist pin 92L and a right load cell 131R is provided on right wrist pin 92R.

Figure 5:
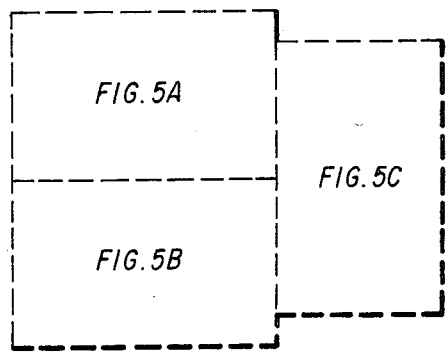
FIG. 5 is a diagrammatic schematic view showing the interrelationship of FIGS. 5A, 5B, and 5C.

The strain gages 124, 126, 128, and 130 shown in the embodiment of FIGS. 3 and 5 are strain gages such as model EA-06-125DW-120 manufactured by MicroMeasurements Division of Measurements Group. Accordingly, the grid pattern of these strain gages has to be oriented at 45 degrees with respect to the major axis 114 of the wrist pin 92 and at 90 degrees with respect to one another. It should be understood, however, that in other embodiments other types of strain gages are usable so long as they are mounted properly.

In the vicinity of the annular recesses 120, 122 radial passageways 132, 134, respectively, are provided whereby cavity 112 communicates with the annular recesses 120, 122, respectively. The passageways 132, 134 accommodate electrical lines which are connected to the strain gages 124, 126, 128, and 130, respectively. Near an end of the wrist pin 92 a cable 136 carries the electrical lines to suitable input (drive) circuitry and suitable output (signal take off) circuitry. Cable 136 is clamped to the end of the wrist 92 by a bracket 138 and a fastener 139.

Figure 4:
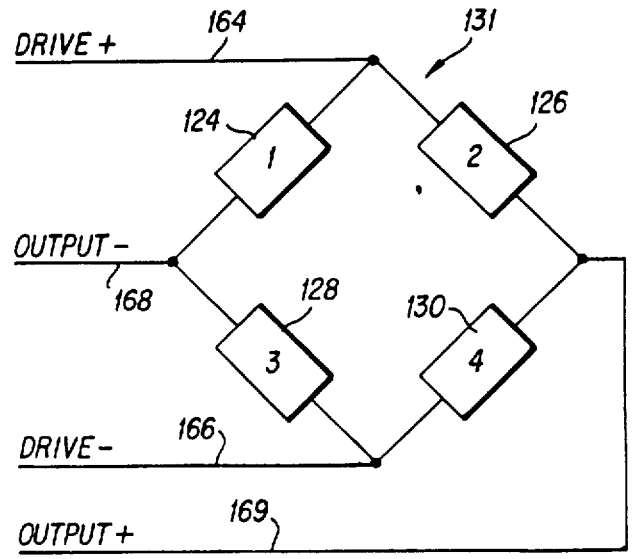
FIG. 4 is a schematic diagram showing the electrical connection of sensors utilized in an embodiment of the invention.

FIG. 4 shows a bridge configuration in which the strain gages 124, 126, 128, and 130 comprising the load cell 131 are connected. Strain gages 124 and 126 are connected to have a common positive phase drive signal applied on a line 164 to their respective input terminals. Likewise, the input terminals of strain gages 128 and 130 are connected together whereby a common negative phase drive signal is applied thereto on line 166. The output terminals of the strain gages 124 and 128 are connected together into a negative phase output line 168. The output terminals of the strain gages 126 and 130 are connected together into a positive phase output line 169. Electrical output signals indicative of the sensed stress are sensed by the strain gages connected in the bridge configuration of FIG. 4 and applied to the output lines.

In the above regard, it is understood that two such bridge circuits are provided, one for the left load cell 131L and one for the right load cell 131R. Accordingly, the left load cell 131L has drive lines 164L, 166L and output lines 168L, 169L; the right load cell has drive lines 164R, 166R and output lines 168R, 169R.

The signal processor 200 (also known as signal drive and output circuitry) is shown in FIG. 5 and comprises a microprocessor 201; an analog-to-digital convertor (ADC) 202; a first parallel interface adaptor (PIA) 204; a second PIA 206; a memory; a digital-to-analog convertor (DAC) 208; a decoder/demultiplexer 210; a first quad operational linear amplifier chip 212 having op amps 212A, 212B, 212C, and 212D; operation amplifiers 214, 215, and 216; a second quad linear operational amplifier chip 218 having op amps 218A and 218B; a first quad 2-input NAND gate chip 220 having NAND gates 220A, 220B, 220C, and 220D; a second quad 2-input NAND gate chip 222 having NAND gates 222A and 222B; a third quad 2-input NAND gate chip 224 having NAND gates 224A, 224B, 224C, and 224D; a quad 2-input NOR gate chip 226 having NOR gates 226A, 226B, 226C, and 226D; a third quad linear operational amplifier chip 228 having op amps 228A, 228B, 228C, and 228D; a dual J-K flip-flop chip 230 chip 230 having J-K flip-flops 230A and 230B; and, NPN transistors 232A, 232B, 232C, and 232D.

Concerning various ones of the chips listed above, chips 212, 218, 228 each have part number 2902; chips 220 and 222 each have part number 74C00; chip 224 has part number 74LS00; chip 226 has part number 74LS02; chip 230 has part number 74C73; and, PNP transistors 232A, 232B, 232C, and 232D each have part number 2N4400.

The signal processor 200 also includes a data bus 236; an address bus 237; a control bus 238; and, a peripheral address bus 239. Included as lines on the control bus 238 are the following: E;$\overline{E}$;$\overline{RES}$;R/W;VMA; $\overline{IRQ}$;$\overline{NMI}$;$\overline{BS0}$,$\overline{BS1}$, . . . $\overline{BS7}$.

Figure 5A:
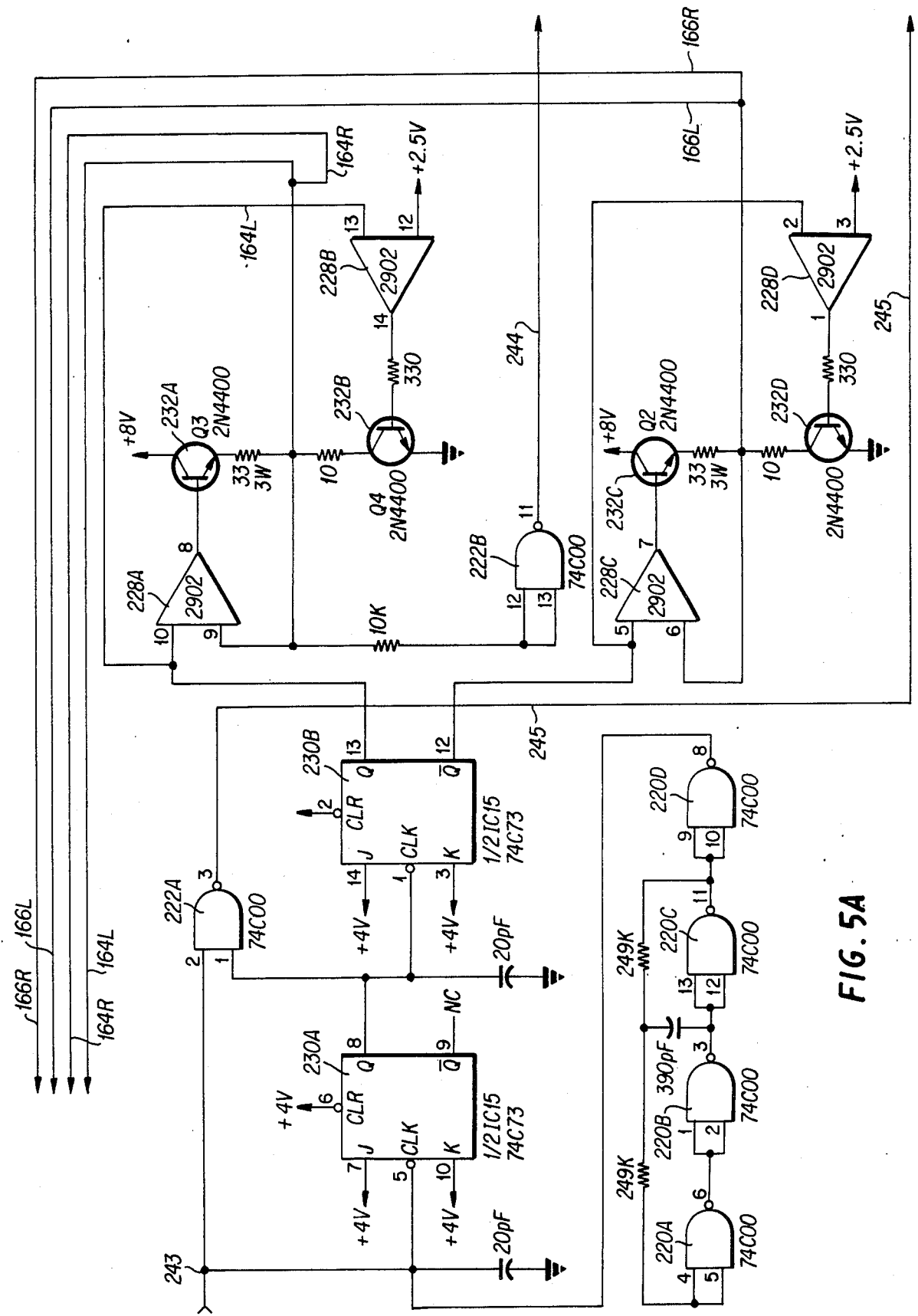
FIGS. 5A, 5B, and 5C are schematic views showing the architecture of signal processing means according to an embodiment of the invention.
Figure 5B:
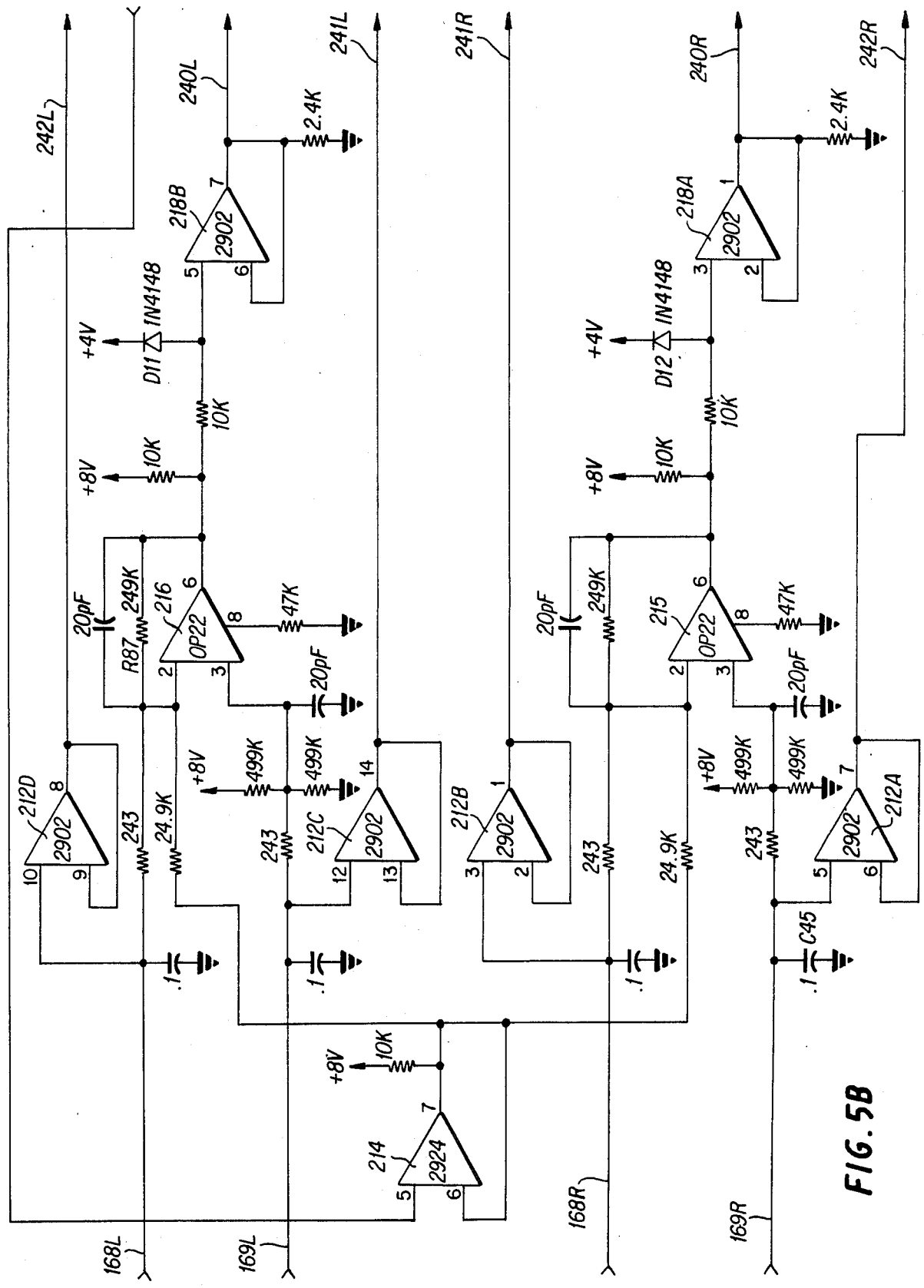
Figure 5C:
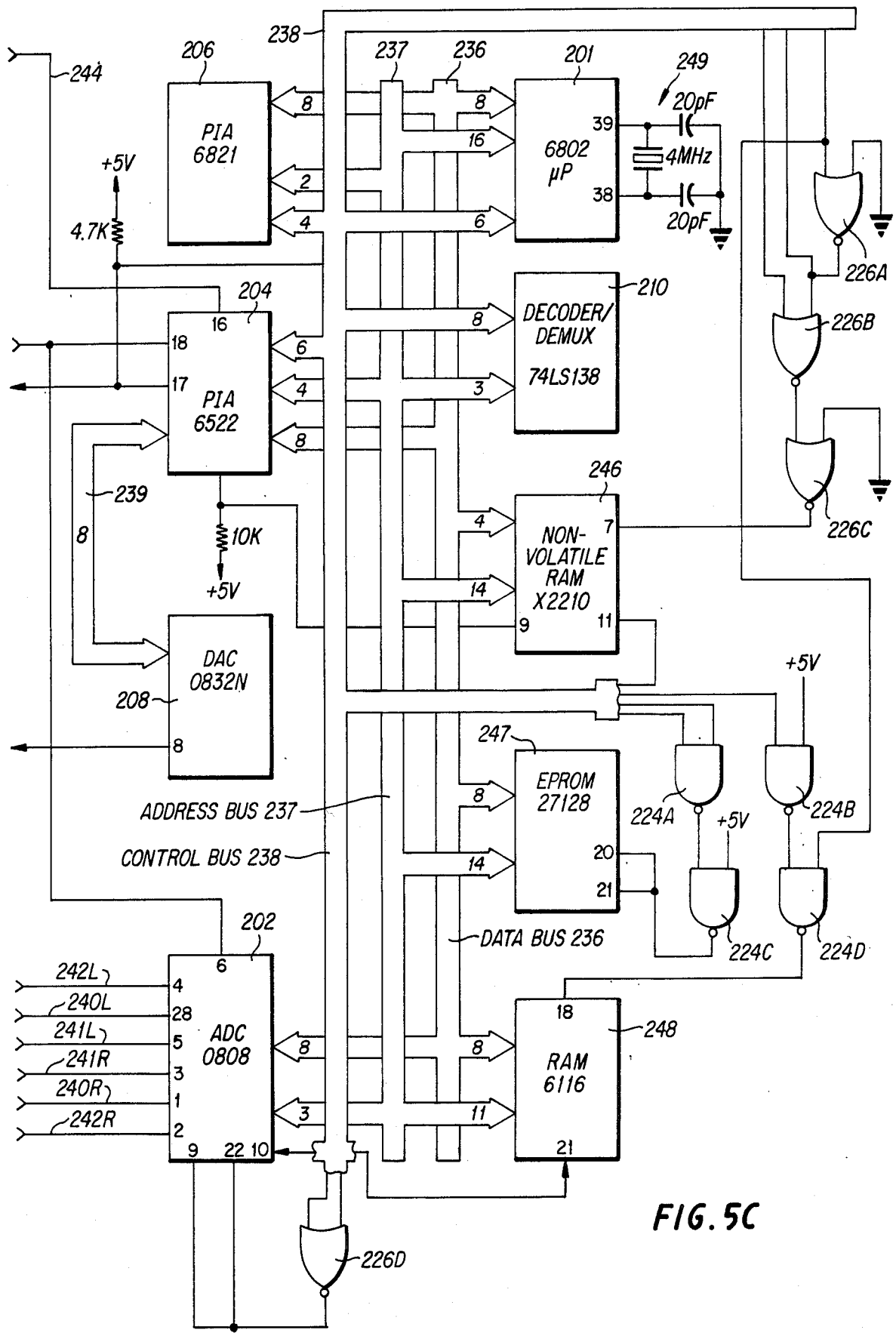

The circuitry shown in FIG. 5B basically serves to receive, amplify, and process signals received from the load cells 131L and 131R before those signals are applied to the ADC 202. In this regard, negative phase and positive phase output signals are received from the right load cell 131R on lines 168R and 169R, respectively; negative phase and positive phase output signals are recieved from the left load cell 131L on lines 168L and 169R, respectively. A resultant right load cell signal is applied to pin 1 of the ADC 202 on line 240R; a resultant left load cell signal is applied to pin 28 of the ADC 202 on line 240L. Signals on lines 241R and 242R are applied to pins 3 and 2, respectively, of ADC 202 for use when testing load cell 131R; signals on lines 241L and 242L are applied to pins 5 and 4, respectively, of ADC 202 for use when testing load cell 131L.

The circuitry shown in FIG. 5A basically serves to drive the strain gage bridges comprising the load cells 131L, 131R. Circuitry in FIG. 5A serves as an oscillator for detetmining the frequency for driving the strain gage bridges. In this regard, point 243 is connected to a conventional voltage doubler circuit (not shown). Lines 164R and 166R, respectively, are the lines upon which the positive and negative phase drive signals are applied to load cell 131R. Likewise, lines 164L and 166L, respectively, are the lines upon which the positive and negative phase drive signals are applied to load cell 131L. Line 244 carries a signal indicative of bridge polarity (i.e. indicative of whether positive phase or negative phase is being applied) and is connected to pin 16 of PIA 204. Line 245 is connected to pin 18 of the PIA 204 and ultimately to pin 6 of the ADC 202 and carries thereon sensor interrupt signals. The sensor interrupt signals carried on line 245 are generated when the circuitry of FIG. 5A has determined that the output signals from the strain gages have sufficiently settled down for the accurate readings thereof.

The microprocessor 201 is a 6802 microprocessor which utilizes two 8-bit accumulators; a 16 bit index register; a 16 bit program counter; a 16 bit stack pointer; and an 8 bit condition code register. Pins 1, 36, and 21 of the microprocessor 201 are connected to ground; pins 2, 3, 8, and 35 are connected to +5 volts; pins 38 and 39 are connected to a 4 MHZ oscillator 249 as shown; pins 33, 32, 31, 30, 29, 28, 27, and 26 are connected to data bus 236; pins 9-20, 22-25 are connected to address bus 237, and pins 40, 37, 34, 4, 5, and 6 are connected to the control bus 238 (pin 4 also being connected to +5 volts through a 4.7K resistor).

The memory of the signal processor 200 comprises a non-volatile RAM 246 (such as XICOR X2210); an EPROM 247 (such as part 27128); and a RAM 248 such as Hitachi 6116).

The analog-to-digital convertor (ADC) 202 is of a type marketed by National as part ADCO808. Pin 26 of the ADC 202 is connected to +12 volts supply; pin 11 is connected to +5 volts; pin 12 is connected to +4 volts; pin 16 is connected to +1 volt; pin 13 is connected to ground; pin 6 is connected ultimately to line 244. Pins 17, 14, 15, 8, 18, 19, 20, and 21 are connected to the data bus 236; pins 23, 24, and 25 are connected to the address bus 237. Pins 9 and 22 are connected to the output terminal of NOR gate 226D, the input terminals of NOR gate 226D being connected to the E and $\overline{BS5}$ lines of control bus 238. The connections to pins 1, 2, 3, 4, 5, and 28 have been earlier described.

The PIA 204 is of a type marketed by Rockwell as part 6522. Pin 1 of the PIA 204 is connected to ground; pin 24 is connected to +5 volts; pins 11, 12, and 13 are each connected to +5 volts through the series combination of a 2.4K resistor and a diode; pin 39 is connected to pin 9 of the non-volatile RAM 246; pin 18 is connected to line 245 (and to pin 6 of the ADC 202); pin 16 is connected to the bridge polarity line 244; pin 17 is connected (1) to the servo valve 61, (2) to +5 volts through a 4.7K resistor, and (3) to the $\overline{NMI}$ line of the control bus 238. Pins 33, 32, 31, 30, 29, 28, 27, and 26 are connected to the data bus 236; pins 35, 36, 37, and 38 are connected to the address bus 237; and, pins 2-9 are connected to the peripheral address bus 239.

The second PIA 206 is of a type manufactured by Motorolla as part 6821. Pin 1 of the PIA 206 is connected to ground; pins 20, 22, and 24 are connected to +5 volts; pins 33, 32, 31, 36, 29, 28, 27, and 26 are connected to the data bus 236; pins 35 and 36 are connected to the address bus 237; pins 21, 23, 25, and 34 are connected to the R/W, $\overline{BS1}$, E, and $\overline{RES}$ lines, respectively of control bus 238. In addition, pin 9 is connected to transmit data to a hereinafter-described operator interface panel 250; pin 4 is connected to receive data from panel 250; and, pin 6 is connected for clocking purposes to the panel 250.

The digital-to-analog convertor (DAC) 208 is of a type marketed by National as DAC0832N. Pins 1, 2, 3, 10, 18, and 17 of the DAC 208 are connected to ground; pins 19 and 20 are connected to +13 volts; pin 11 is connected to +4 volt; pin 12 is connect to +1 volts; pins 7, 6, 5, 4, 16, 15, 14, and 13 are connected to the peripheral address bus 239; pin 8 is connected to input pin 5 of the op amp 214 of FIG. 5B.

The Decoder/Demultiplexer 210 has pins 4, 5, and 8 connected to ground; pin 16 connected to +5 volts; pins 1, 2, and 3 connected to address bus 237; and, pins 15 ($\overline{BS0}$), 14 ($\overline{BS1}$), 13 ($\overline{BS2}$), 12 ($\overline{BS3}$), 11 ($\overline{BS4}$), 10 ($\overline{BS5}$), 7 ($\overline{BS7}$), and 6 (VMA) connected to the control bus 238.

The non-volatile RAM 246 has pin 8 connected to ground; pin 18 connected to +5 volts; pins 12-15 connected to data bus 236; pins 6, 5, 4, 3, 16, 2, 17, 1 connected to address bus 237; pin 11 connected to the R/W line of control bus 238; and, pin 9 connected to pin 39 of PIA 204.

The EPROM 247 has pins 1, 27, and 28 connected to +5 volts; pin 14 connected to ground; pins 11-13, 15-19 connected to data bus 236; pins 10, 9, 8, 7, 6, 5, 4, 3, 25, 24, 21, 23, 2, and 26 connected to the address bus 237; and, pins 20 and 21 connected to the output terminal of NAND gate 224C.

The RAM 248 has pins 12 and 20 connected to ground; pin 24 connected to +5 volts; pin 18 connected to the output terminal of NAND 224D; pins 9-11, 13-17 connected to data bus 236; pins 8, 7, 6, 5, 4, 3, 2, 1, 23, 22, 19 connected to the address bus 237; and, pin connected to the R/W line of control bus 238.

The NOR gate 226A has one input terminal thereof connected to ground and the other input terminal connected to the E line of control bus 238. The output terminal of NOR gate 226A is connected to the $\overline{\text{E}}$ line of control bus 238 as well as to a first input terminal of NOR gate 226B. A second input terminal of NOR gate 226B is connected to the $\overline{\text{BS4}}$ line of the control bus 238.

Figure 6:
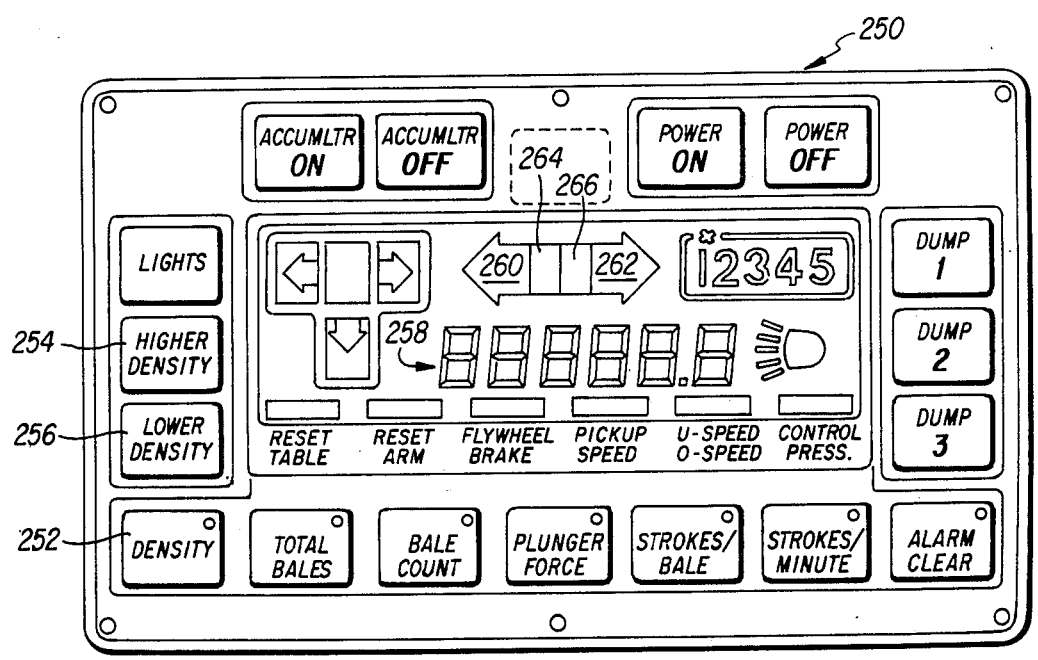
FIG. 6 is a front view of an interface panel provided with an agricultural baling apparatus according to an embodiment of the invention.

FIG. 6 shows an operator interface panel 250 which includes thereon various control keys and displays. Aspects of the operator interface panel pertinent to the instant invention include a density key 252; a higher density key 254; a lower density key 256; a digital readout display 258; a leftwardly pointing arrow display 260; a rightwardly point arrow display 262; and, display boxes 264 and 266 located between the arrow displays 260 and 262.

With regard to the operator interface panel 250, to examine a previously-input density set point value an operator momentarily hits the density key 252 whereup a value in the range of 0 to 99 appears on the digital readout display 258. To change that density set point, the operator momentarily hits the higher density key 254 or the lower density key 256 to scroll the setting up or down respectively by one digit. For example, the operator may desire to set the density set point value at 55 when baling a crop such as alfalfa.

The signal processor 200 is programmed with routines of coded instructions whereby the signal processor 200 receives the AC signals produced by the left load cell 131L (comprisings sensors 124L, 126L, 128L, and 130L) and the right load cell 131R (comprising sensors 124R, 126R, 128R, and 130R); processes and analyzes values corresponding to the load cell signals; and, generates a pulse width modulated control signal for application to the servo valve 61 comprising the tension adjusting system unit 60 (which governs the tension applied to the bale case rails 54 and 56). In addition, the signal processor 200 is programmed with routines of coded instructions which facilitate input and output operations with an operator, including output display operations such as those depicted on the operator interface panel 250.

The routines with which the signal processor 200 is programmed are loaded into memory, particularly into EPROM 247. Pertinent ones of the routines described hereinafter include routines MAIN, IRQT, LOOP, ANALYSIS, NMIR, and BLSH.

ROUTINE MAIN

Figure 7:
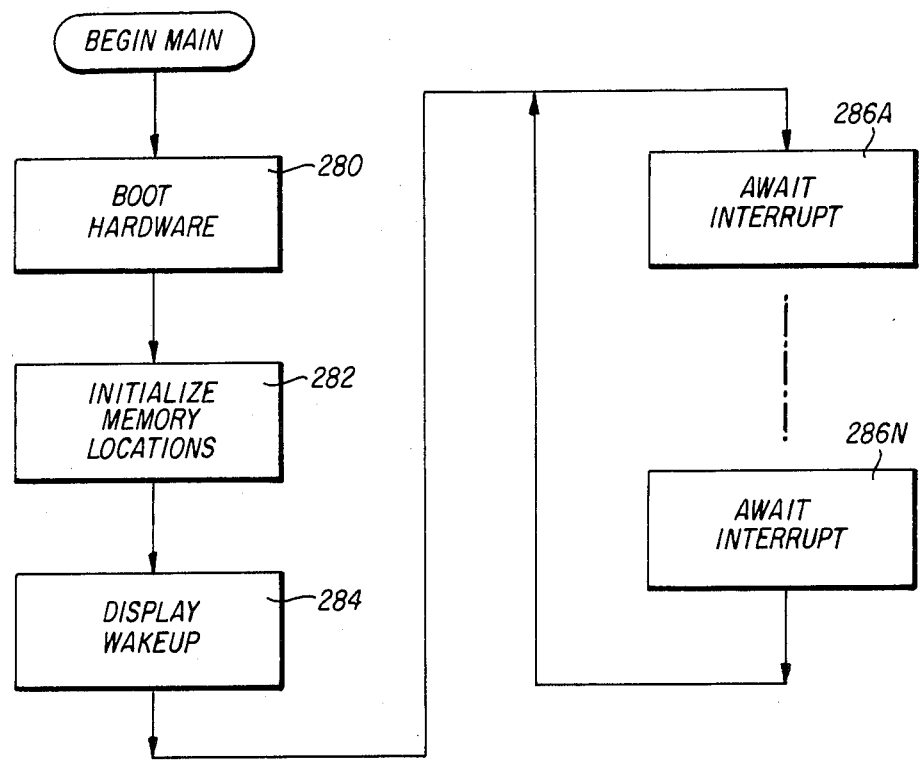
FIG. 7 is a diagrammatic schematic view showing processing steps associated with a routine MAIN executed by signal processing means.

Basic processing steps associated with the routine MAIN are shown in FIG. 7. Generally, the routine MAIN serves to boot system hardware (step 280); to initialize various memory locations (step 282); and, to wake up displays including various operator interface panel (250) displays (step 284). Thereafter the routine MAIN basically interfaces with the operator through the operator interface panel 250 for display and input purposes and awaits interrupts (steps 286A through 286N) which basically serve to direct processing to one or more routines. The two primary types of interrupts described hereinafter are sensor interrupts (which occur about every 500 microseconds) and non-maskable interrupts (which are generated about every 2.5 milliseconds). Processing of routine MAIN continues in loop-like fashion until the signal processor 200 is turned off.

Output signals from the left and right load cells 131R and 131L prompt the execution of a routine IRQT. In this regard, sensor interrupts on line 245 are grouped in sets of four with the interrupts in each set being in a predetermined order. In a given set of sensor interrupts, a first interrupt corresponds to a positive phase signal on line 169R from the right load cell; the second interrupt corresponds to a negative phase signal on line 168R from the right load cell; the third interrupt corresponds to a positive phase signal on line 169L from the left load cell; and, the fourth interrupt corresponds to a negative phase signal on line 168L from the left load cell. The magnitude of the voltage signal from load cell 131R is applied to ADC 202 on line 240R; the magnitude of the voltage signal from load cell 131L is applied to the ADC 202 on line 240L. The value on line 244 provides an indication of the polarity (whether positive or negative phase).

As seen hereinafter, when the signal processor 200 has received digitally converted sensor output signals (expressed in terms of voltage) for both positive and negative phases of a given load cell, the signal processor 200 determines the difference between the positive and negative phase signal magnitudes and uses the same as an indication of the stress currently experienced by that load cell.

ROUTINE IRQT

Figure 8:
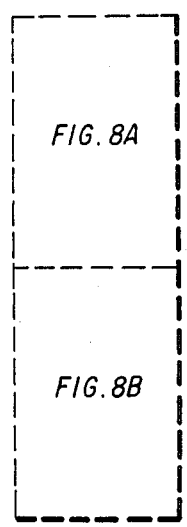
FIG. 8 is a diagrammatic schematic view showing the interrelationship of FIGS. 8A and 8B.

FIG. 8 shows steps executed by the signal processor 200 in connection with the routine IRQT. A first such set (step 300) involves a determination whether the sensor interrupt is from the left load cell 131L or the right load cell 131R. Depending upon the result of the determination of step 300, execution jumps to one of two branches of steps. Inasmuch as the two branches of steps are similar (one branch being applicable to an interrupt associated with the right load cell 131R and the other branch being applicable to an interrupt associated with the left load cell 131L) similar steps of the two branches are given the same numerical reference numbers. The reference numbers are, however, followed by a suffix "R" to represent steps executed in connection with the interrupt from the right load cell 131R. Reference numerals associated with steps executed in connection with interrupts from the left load cell of 131L are given the suffix "L".

It will be recalled from the foregoing that the sensor interrupts are grouped in sets of four with the interrupts in each set being in a predetermined order as described above. For the sake of simplification, the current discussion assumes that the first two interrupts of a given sensor interrupt set have already been received and that the two remaining interrupts of the set have yet to be processed. That is, both the positive phase and the negative phase signals from the right load cell 131R have been received and at least partially processed (in a manner understood by analogy from the ensuing discussion of the interrupts from the left load cell 131L), and that the just-received interrupt was determined at step 300 to be associated with the left load cell 131L.

Having determined the load cell to which the signal interrupt pertains, the routine IRQT at step 302 determines whether the phase of the signal is positive or negative. The polarity of the signal is determined on the basis of the signal applied on line 244. If the polarity is positive, the magnitude of the sensor signal applied on line 240L to ADC 202 is stored at step 304 for eventual comparison with the magnitude of the upcoming negative phase signal for the same load cell. Thereafter routine IRQT awaits the next sensor interrupt which, according to the predetermined order, which will indicate the availablity of the negative phase signal for the left load cell 131L.

When a sensor interrupt occurs in connection with the negative phase signal of the left load cell 131L, the tests at steps 300 and 302 of routine IRQT result in the storage at step 306 of the magnitude of the negative phase signal of the left load cell 131L. With the routine IRQT then having values corresponding to the magnitudes of the positive phase and negative phase AC signals from the left load cell 131L, at step 308 routine IRQT determines the actual loading on the left conrod cell 131L by finding differential between the magnitude of the positive phase and negative phase signals.

Having determined the actual loading on the left conrod cell by finding the differential between the magnitude of the positive and negative phase signals associated with this interrupt set, at step 310 the routine IRQT adjust the just-determined left conrod loading value for digit offset. In this respect, it is understood that the AC 208 feeds to the amplifier 214 a signal whereby operation of amplifier 214 is kept within its usable range. The digit offset value added at step 310 corrects minor inacuracies introduced as a result of the feedback from the DAC 208 to the amplifier 214.

At step 312 the routine IRQT enters the adjusted left conrod current loading value into a left conrod moving average buffer. In this regard, the routine IRQT first uses a stored pointer to determine the location of the left conrod moving average buffer. Another pointer is used for storing the adjusted left conrod current loading value into an appropriate location in the moving average buffer, after which this second pointer is incremented. If incrementation of the second pointer causes the second pointer to reach the end of the buffer, the second pointer is then set to the top of the buffer. In the embodiment described herein, eight memory locations are included in the left conrod moving average buffer, meaning that the eight-most recent adjusted left conrod loading values are stored therein.

At step 314 the routine IRQT computes a new average signal value from the left conrod moving average buffer. In this respect, routine IRQT adds the values in each of the eight moving average buffer locations; divides the sum by the number eight; and, stores the moving average at a designated memory location.

ROUTINE ANALYSIS

Figure 10:
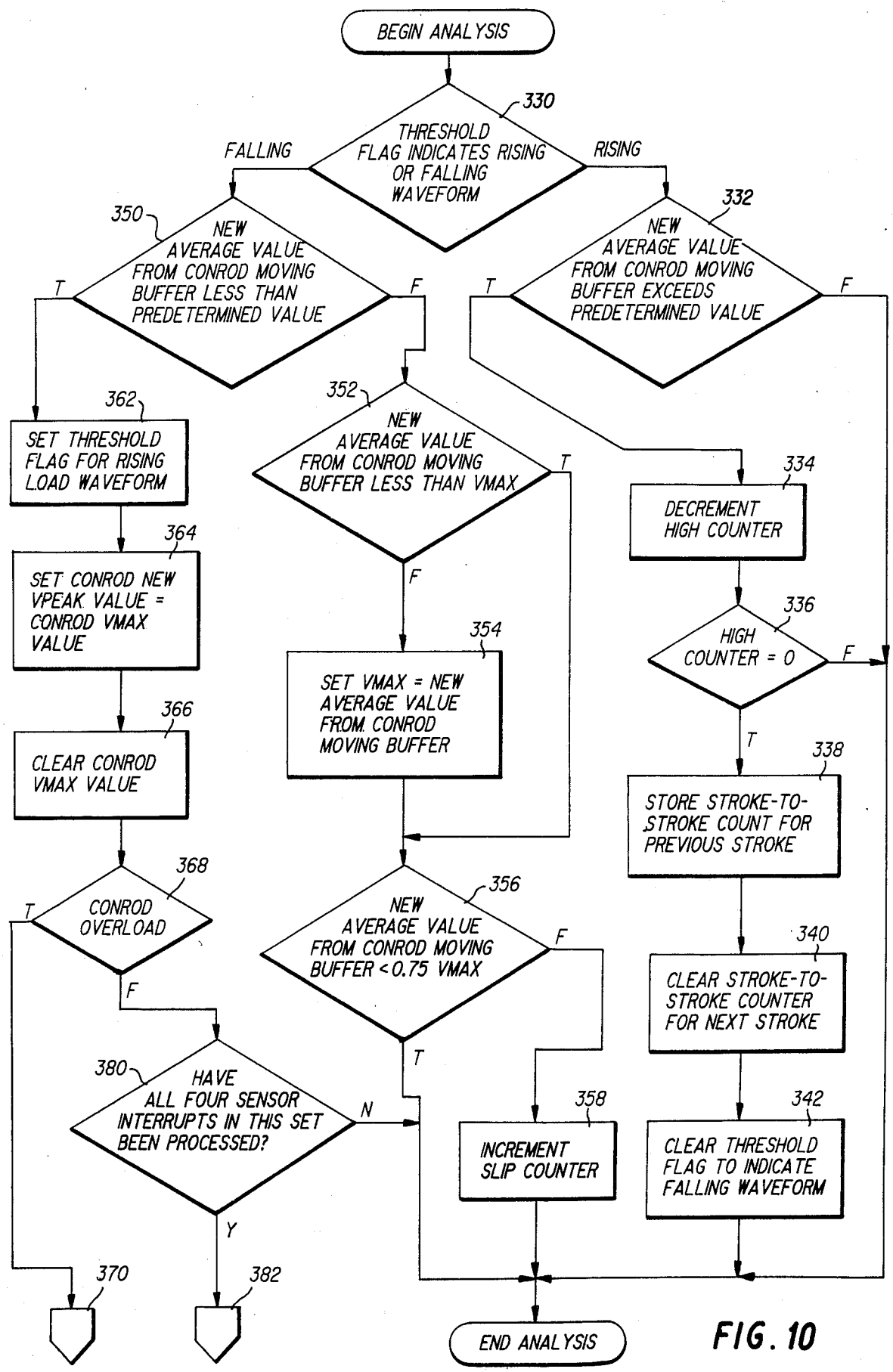
FIG. 10 is a diagrammatic schematic view showing processing steps associated with a routine ANALYSIS executed by signal processing means.

Having computed a current moving average value from the left conrod moving average buffer, routine IRQT passes control to a routine ANALYSIS which includes processing steps such as those indicated in FIG. 10. The processing steps depicted in FIG. 10 for routine ANALYSIS are shown generically without descrimination whether the current signals are being processed from the left load cell 131L or the right load cell 131R, it being understood that similar steps are provided with respect to both the right load cell 131R and the left load cell 131L. The reader will recall that the current discussion involves the processing of signals just received from the left load cell 131L, and the discussion with respect to the left load cell signal is continued hereinafter.

The routine ANALYSIS checks the value of a flag THRESHOLD to determine whether the waveform based upon by previous average values from the left conrod moving average buffer is rising or falling. In this regard, routine ANALYSIS checks at step 330 to see if the flag THRESHOLD is set, thereby indicating a rising waveform. If flag THRESHOLD is not set, a falling waveform is indicated.

In the event of a rising waveform, routine ANALYSIS checks at step 332 to determine whether the new (i.e. most recent) average value calculated from the conrod moving buffer exceeds a predetermined value, the predetermined value in the embodiment under discussion being on the order of 12. If the new average value does not exceed the predetermined value, routine ANALYSIS simply completes its processing. On the other hand, if the predetermined value is exceeded by the new average value from the conrod moving buffer, a counter known as HIGH COUNTER, having been previously set to a predetermined value, is decremented (step 334). By decrementing the counter HIGH COUNTER down to zero, the routine ANALYSIS is able to ensure that a sufficient number of new average values from the conrod moving buffer have been found to exceed the predetermined value referred to in step 332. Thus, when it has been confirmed at step 336 that the counter has decremented down to zero, the routine ANALYSIS is prepared to both mark the end of a previous plunger stoke and mark the beginning of a new plunger stroke. In this respect, at step 338 the routine ANALYSIS stores a value from a stroke-to-stroke counter in an appropriate memory location for use as a stroke-to-stroke count for the previous plunger stroke. Routine ANALYSIS then clears the stroke-to-stroke counter so that the counter can be incremented with respect to signals associated with the next plunger stroke. Moreover, at step 342 the routine ANALYSIS clears the flag THRESHOLD to indicate that it is expected that the waveform appearance will thereafter be generally a falling waveform. Having cleared the flag THRESHOLD, routine ANALYSIS then completes its processing with respect to this new average value from the conrod moving buffer.

If the check of the flag THRESHOLD at step 330 reveals that the waveform is currently generally falling, a check is made at step 350 whether the new average value from the conrod moving buffer is less than a predetermined value which, in the illustrated embodiment, is on the order of 8. If the new average value from the conrod moving buffer is not less than the predetermined value, two further checks are made. In this regard, a first further check at step 352 involves a determination whether the new average value from the conrod moving buffer is less than the current value stored at a location VMAX. If the new average value from the conrod moving buffer is not less than VMAX, the new average value from the conrod moving buffer is stored at the location VMAX (step 354).

The second further check involves a determination at step 356 whether the new average value from the conrod moving buffer is less than 0.75 times the value currently stored at the location VMAX. If the test performed at step 356 is negative, a a slip counter (either the counter LEFT SLIP or the counter RIGHT SLIP, depending on which load cell waveform is being analyzed) is incremented at step 358 before routine ANALYSIS completes its processing with regard to the current average value from the conrod moving buffer. Thus, it is seen that in analyzing a waveform for a given load cell, the routine ANALYSIS determines sensor voltage peaks from the average values from the conrod moving buffer for the given load cell and, so long as the currently sensed voltage signal is within a predetermined neighborhood of the sensor voltage peak, updates the appropriate slip counter. The counter SLIP COUNTER is used as an indication for both the degree of bale slippage through the bale case and for the quantity of crop material being ingested into the bale case. In this regard, by observing sensor output voltage signal waveforms it has been noted that following a voltage peak a voltage plateau is formed before the voltage tapers off significantly, and that the duration of this plateau corresponds substantially to the degree of bale slip which occurs in the bale case following the application of compactive force by the plunger.

In the event that the test performed at step 350 indicates that the new average value from the conrod moving buffer is less than the predetermined value referenced at step 350, at step 362 the routine ANALYSIS sets the flag THRESHOLD for a generally rising load waveform. In addition, at step 364 the current value at the location VMAX is also loaded into a location VPEAK and, at step 366, the contents of the location VMAX is cleared.

After establishing a new value for location VPEAK for the load cell, at step 368 the routine ANALYSIS checks to determine whether the new VPEAK value is of sufficient magnitude as to indicate a conrod overload. In this regard, for the embodiment under discussion, a VPEAK value on the order of 120 is sufficient to indicate a conrod overload. If a conrod overload is detected in this manner at step 368, execution jumps as indicated by connector symbol 370 to a location in routine LOOP. As seen hereinafter with respect to a detailed discussion of the routine LOOP, upon overload detection, a value stored at location PREVIOUS PWM is essentially halved with the result that the tension applied to the bale case rails is significantly reduced to rectify the conrod overload.

After checking at step 368 for a conrod overload, the routine ANALYSIS checks at step 380 to determine whether all four sensor interrupts in this related set have been processed. If so, execution jumps to a location in routine LOOP denoted by the connector symbol 382. Otherwise, the routine ANALYSIS completes its processing.

As mentioned before, the routine ANALYSIS is performable with respect to signals from both the left load cell 131L and signals from the right load cell 31R. Thus, it is understood that there are both left and right stroke-to-stroke counters (namely, counters LEFT STROKE-TO-STROKE and RIGHT STROKE-TO-STROKE), both left and right "VMAX" locations (namely, LEFT CONROD VMAX and RIGHT CONROD VMAX), both left and right "VPEAK" locations (namely, LEFT CONROD VPEAK and RIGHT CONROD VPEAK), left and right slip counters LEFT SLIP and RIGHT SLIP, and so forth.

Unless execution of the routine ANALYSIS results in a jump to routine LOOP as indicated by symbols 370 and 372, upon the completion of routine ANALYSIS execution returns to routine IRQT, and particularly to step 390 of routine IRQT. In view of the current discussion concerning a signal from the left load cell 131L, execution returns to step 390L whereat the counter LEFT STROKE-TO-STROKE is incremented. Thereafter at step 392 a determination is made whether the value in the counter LEFT STROKE-TO-STROKE is within proper limits. In this regard, if the value in the counter LEFT STROKE-TO-STROKE exceeds a maximum permissible value, the contents of the counter LEFT STROKE-TO-STROKE is set to the maximum permissible value. Then, and since both left and right stroke-to-stroke counters are being maintained, at step 394 the contents of the counters LEFT STROKE-TO-STROKE and RIGHT STROKE-TO-STROKE are summed and stored in a location STROKE-TO-STROKE.

Upon completion of step 394 the routine IRQT ends its processing. In like manner as hereinbefore described, upon the receipt of the next sensor interrupt the routine IRQT will then be processed in accordance with the particular conrod load cell and polarity associated with the next sensor interrupt.

ROUTINE LOOP

Figure 9:
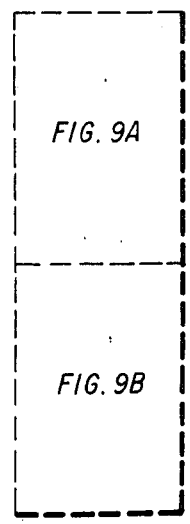
FIG. 9 is a diagrammatic schematic view showing the interrelationship of FIGS. 9A and 9B.
Figure 8A:
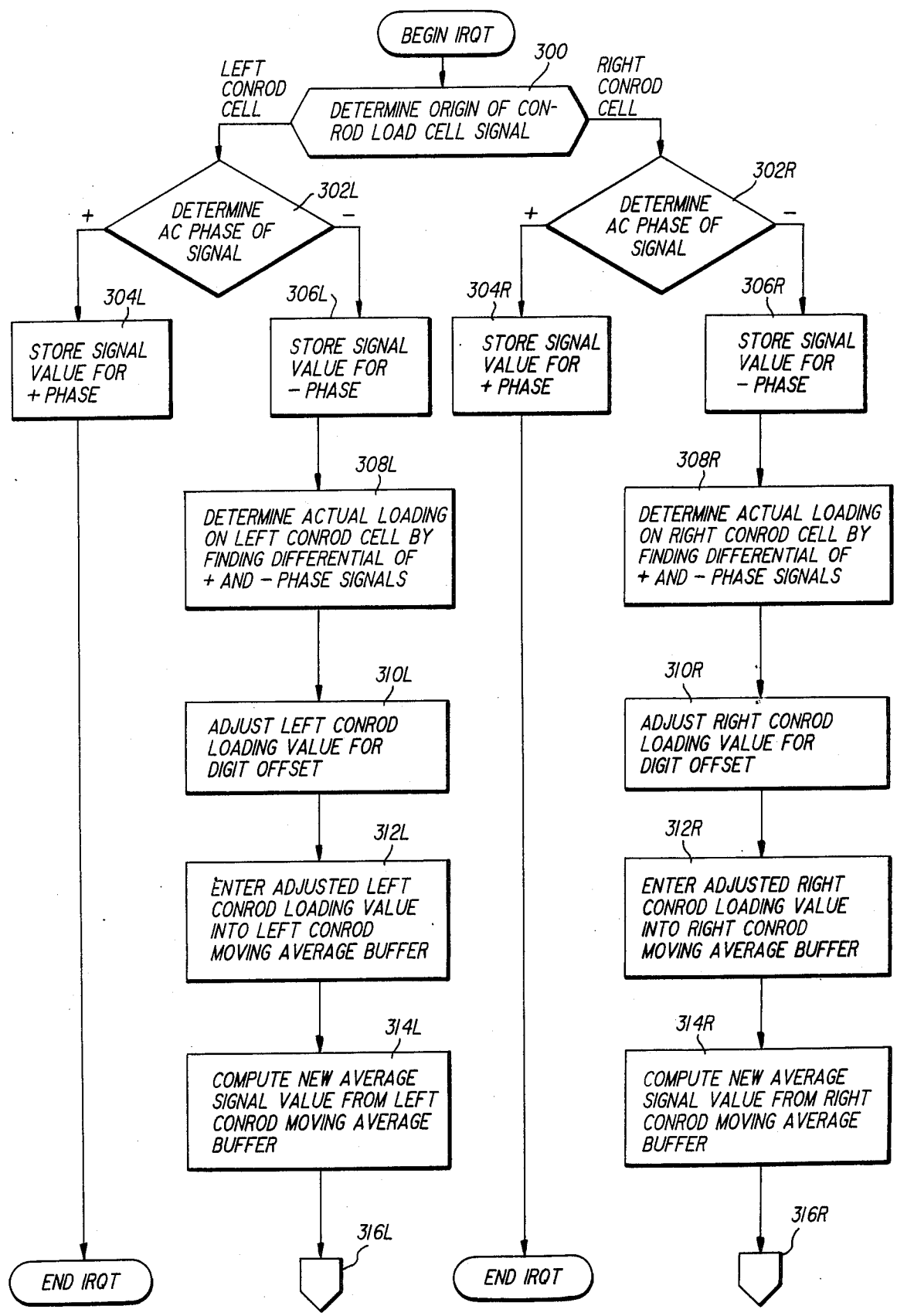
FIGS. 8A and 8B are diagrammatic schematic views showing processing steps associated with a routine IRQT executed by signal processing means.
Figure 8B:
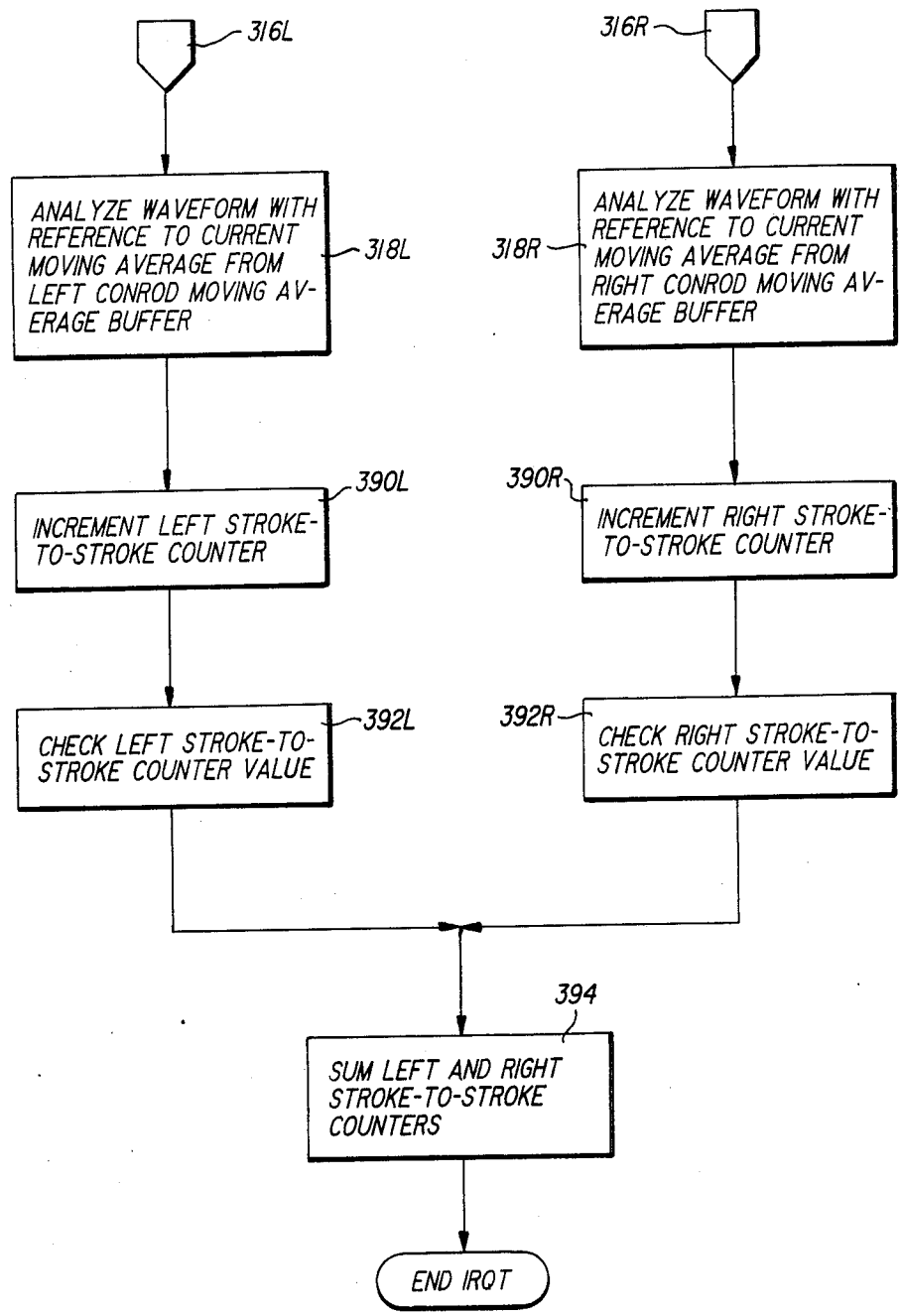
Figure 9A:
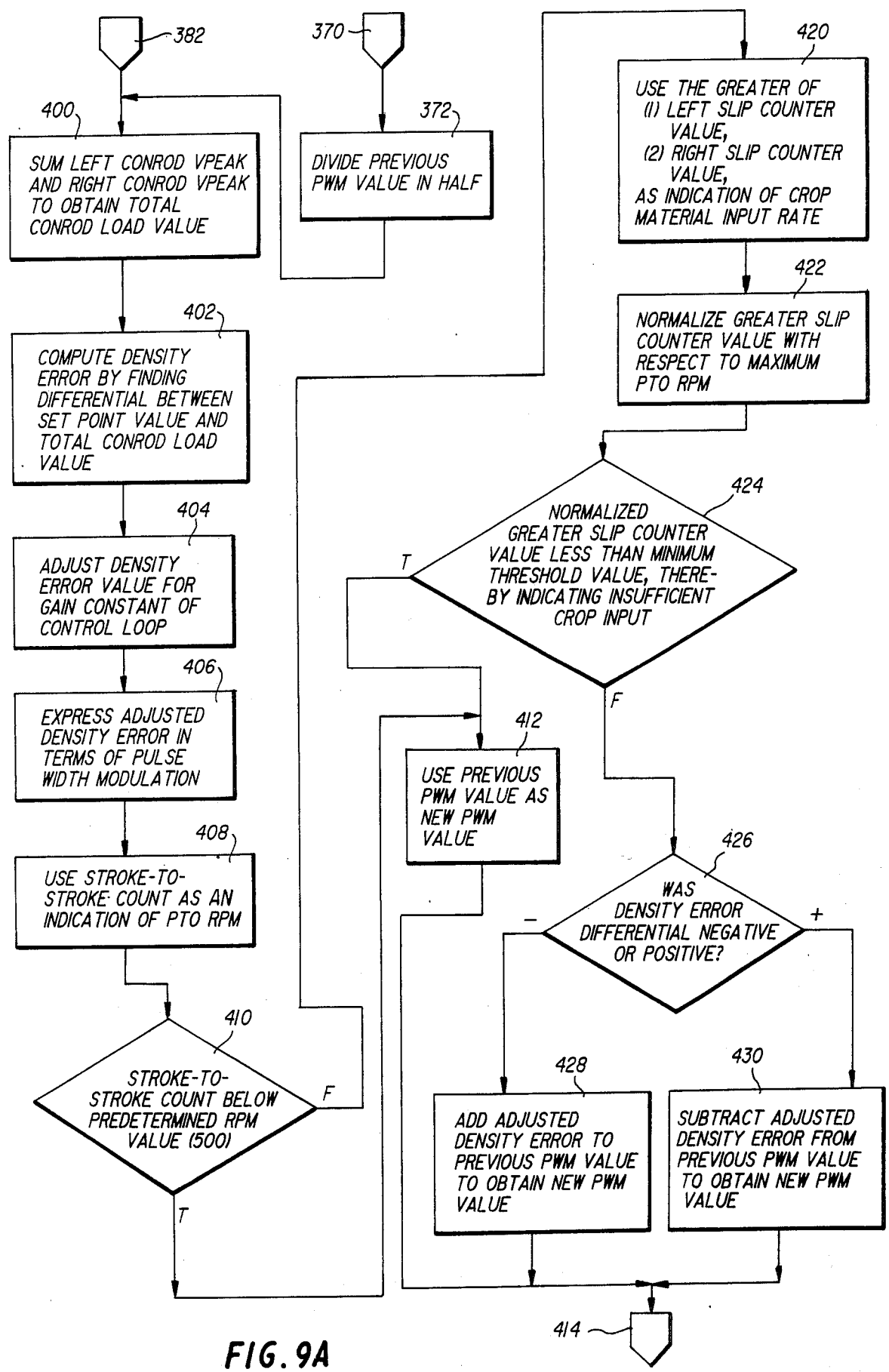
FIGS. 9A and 9B are diagrammatic schematic view showing processing steps associated with a routine LOOP executed by signal processing means.
Figure 9B:
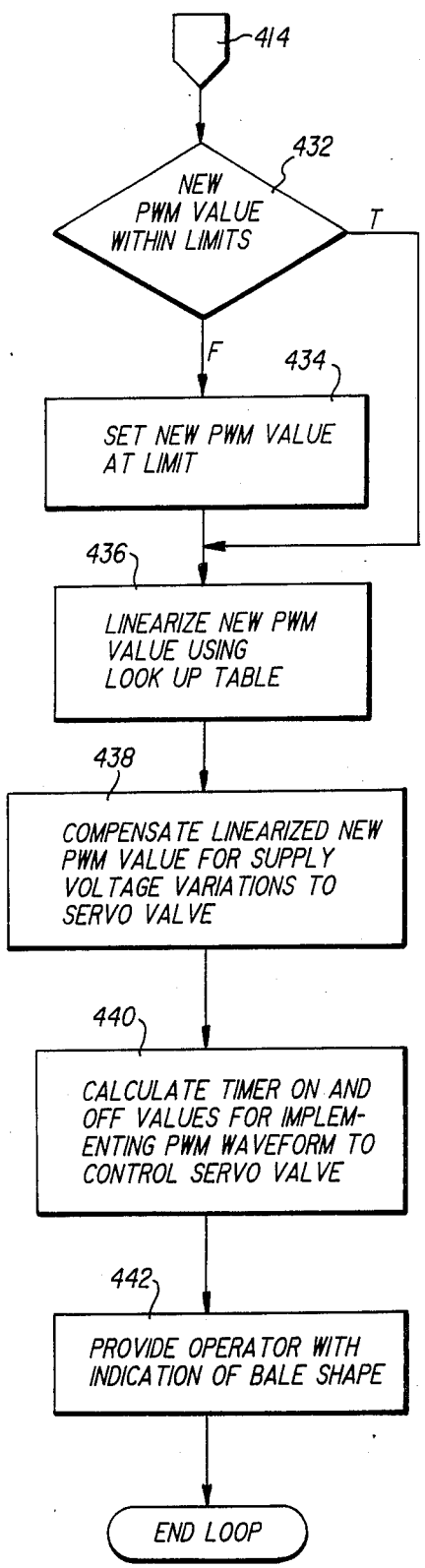

Processing steps associated with the routine LOOP are shown in FIG. 9. Routine LOOP is entered in one of two ways: (1) when the routine ANALYSIS has detected a conrod overload at step 268; and, (2) when routine ANALYSIS has determined at step 380 that all four sensor interrupts for a particular sensor interrup set have been processed. In the event of a conrod overload, before executing the steps described hereinafter the routine LOOP at step 372 divides the value at stored memory location PREVIOUS PWM by a factor of two. From the ensuing discussion it will be understood that the value at location PREVIOUS PWM is used in the determination of a new value to be stored at location NEW PWM, and that the magnitude of the value at location NEW PWM is used in generating the control signal applied to the servo valve 61.

Routine LOOP obtains a total conrod load value at step 400 by summing the values at locations LEFT CONROD VPEAK and RIGHT CONROD VPEAK and storing the result as location COMPUTED TOTAL CONROD LOAD. Routine LOOP then computes a density error value by finding at step 402 the difference between the user-input set point value and the value at location COMPUTED TOTAL CONROD LOAD. In this regard, it will be recalled that the set point value is the user-input value which ranges between 0 and 99 and is an indication of the desired density of the bales being discharged from the baling machine. For the example under discussion it is previously been mentioned that the value 55 can be input as the set point value for alfalfa crop material, for example. In the illustrated embodiment, the desired total conrod loading is calculated as being equivalent to the expression $(SP \times 1.6) + 40$, wherein SP is the set point value which is currently illustrated as being 55. Thus, for the present example, the desired conrod loading value is 128, which corresponds to a source of approximately 44,800 pounds. The desired conrod loading value of 128 is compared to the value at location COMPUTED TOTAL CONROD LOAD and the difference is stored in the location DENSITY ERROR in accordance with step 402.

At step 404 the value stored at location DENSITY ERROR is adjusted to take into consideration the gain constant of the control loop (i.e. the feedback loop including the DAC 208 and the amplifier 214). For the presently described embodiment the gain constant is "1".

At step 406 the routine LOOP reformats the value stored at location DENSITY ERROR so that the value can be represented in terms of pulse width modulation.

In this regard, in reformating the value at location DENSITY ERROR two words of memory are used. One of the words in this location has stored therein a representation of the integer value of the adjusted density error, while the other word has stored therein a representation of the fractional value.

At step 408 the routine LOOP obtains the value stored at location STROKE-TO-STROKE and uses that value as an indication of the PTO speed (PTO RPM). It will be recalled from the previous discussion that the number of counts stored in the counter STROKE-TO-STROKE between wavelength peaks is an indication of the PTO speed. In this regard, the higher the value stored in the counter STROKE-TO-STROKE, the slower is the PTO speed. Having obtained such an indication, at step 410 routine LOOP checks to determine whether the PTO speed (as indicated by the value in counter STROKE-TO-STROKE) is below 500 RPM. If the PTO speed is below 500 RPM, routine LOOP precludes any further change in the tension applied to the bale case rails 54, 56 by a setting (at step 412) location NEW PWM equal to the value stored at location PREVIOUS PWM. Hence, the value at location PREVIOUS PWM is used as the location NEW PWM value and processing jumps to a location indicated by connector symbol 414.

If the PTO speed is determined at step 410 to be above 500 RPM, at step 420 routine LOOP 420 uses the value in either counter LEFT SLIP or counter RIGHT SLIP, whichever is greater, as an indication of the crop material input rate. In this respect it is recalled from the foregoing that the duration of a voltage plateau following a voltage peak substantiall corresponds to the degree of bale slip which occurs in the bale case following the application of compactive force by the plunger, and that the degree of bale slip has further been observed as corresponding to the quantity of crop material being introduced into the bale case. The values in the counters LEFT SLIP and RIGHT SLIP are used as expressions of the durations of the voltage plateau and thus of both the bale slip and quantity of crop material input.

In view of the fact that the degree of bale slippage is also a function of the PTO speed, at step 422 routine LOOP normalizes the slip count value obtained from step 420 with respect to the PTO speed. In this regard, at step 422 the routine LOOP normalizes the greater slip count with respect to the maximum PTO RPM. The normalization at step 422 involves determining at what percent of maximum PTO RPM the baling machine is currently operating and deriving therefrom a compensation factor which is multiplied by the greater slip count. For example, if the maximum PTO RPM is 1150, and the current PTO operating speed as determined with reference to counter STROKE-TO-STROKE is 920, then the appropriate compensation factor is related to the value 0.80.

After normalizing the greater slip count at step 422, at step 424 the routine LOOP checks to determine whether the crop material input to the bale case is at such an adequate level as to preclude further adjustment of the tension on the bale case rails. In this regard, at step 424 a determination is made whether the normalized greater slip counter value is less than a minimum threshold value on the order of 18. If the test at step 424 is affirmative, thereby indicating insufficient crop input, routine LOOP branches to step 412 whereat the value at location PREVIOUS PWM is moved into the location NEW PWM for further processing which continues at the location indicated by connector symbol 414.

The test conducted by routine LOOP at step 424 is significant in protecting the conrods against overload. Consider, for example, what would otherwise happen if the bale case rails 54, 56 were under considerable tension as the baling machine moves to the end of a windrow. Upon entering the head lands the quantity of crop input would significantly decrease and, without the benefit of step 424, the signal processor 200 would seek to keep bale density constant by applying even greater tension to the bale case rails 54, 56. However, upon entering the next windrow the quantity of crop input would immediately increase and would overload the conrods associated with the plunger which is now operating in a more highly tensioned bale case. Thus, step 424 rectifies this potential problem by insuring that bale base 20 is being provided with sufficient crop input flow prior to the adjustment of the tension on the bale case rails 54, 56.

Having determined at step 424 that the quantity of crop input into the bale case is sufficient for permitting further adjustment of the tenison on the bale case rails 54, 56, the routine LOOP begins at step 426 to determine how the tension on the bale case rails 54, 56 is to be changed. In this regard, at step 426 routine LOOP determines whether the value at location COMPUTED TOTAL CONROD LOAD exceeded the user-input set point value. If the determination is negative, at step 28 routine LOOP computes a new value for location NEW PWM by adding the values stored at locations PREVIOUS PWM and DENSITY ERROR. On the other hand, if the result of the determination is positive, at step 430 the routine LOOP computes a new value of location NEW PWM by substracting the value at location DENSITY ERROR from the value at location PREVIOUS PWM. In this regard, it is understood herein that "PWM" locations are actually two locations, one word being associated with a representation of an integer value while the other word is a representation of a fractional value.

Upon reaching a location represented by connector symbol 414, routine LOOP is prepared to further operate upon the new value stored at location NEW PWM. During normal processing a value at location NEW PWM has just been computed to take into consideration the adjusted DENSITY ERROR. Otherwise, if it has been determined (as at step 410) that the PTO RPM value is insufficient, or if it has been determined (as at step 424) that an insufficient quantity of crop material were being introduced into the bale case, the value at location NEW PWM would merely be that previously stored location PREVIOUS PWM.

At step 432 routine LOOP checks to ensure that the value at location NEW PWM is within acceptable limits, particularly if the value is less than 255. If the value at location NEW PWM is not within an acceptable limit, the location NEW PWM is loaded at step 434 with a value representative of the acceptable limit.

At step 436 the routine LOOP linearizes the value at location NEW PWM by using a look-up table. The linearization at step 420 is essentially accomplished by fetching the address from memory which corresponds to the beginning location of the look-up table; adding to the beginning address a value corresponding to the value at location NEW PWM; and, using the contents of the address specified by the thusly-obtained sum as the linearized value. Henceforth it is understood that the value stored at location NEW PWM has been linearized.

Having completed the linearization of step 436, routine LOOP then compensates the value stored at location NEW PWM to take into consideration supply voltage variations to the servo valve. The compensation is represented by step 438.

At step 440 the routine LOOP calculates values for locations TIMER ON and TIMER OFF. As seen hereinafter with reference to routine NMIR, the values at location TIMER ON and TIMER OFF are utilized for implementing a pulse width modulation scheme relative to the signal which controls the servo valve 61. Processing associated with step 440 first involves checking to determine whether the compensated and linearized value at location NEW PWM is within acceptable limits. In this respect, in the illustrated embodiment the minimum and maximum allowed values for location NEW PWM are 4 and 252, respectively. If in excess of 252, the value at location NEW PWM is set to 252. Likewise, if less than 4, the value at location NEW PWM is set at 4.

Also in connection with step 440, the routine LOOP mulitplies the value at location NEW PWM by a factor of 10 and stores the mutiplication result in the location TIMER ON. Knowning that the control signal to the servo valve have a period corresponding to 2.5 milliseconds, the routine LOOP subtracts the value at location TIMER ON from the value 2550 and stores the result at location TIMER OFF. Thus, if the value at location NEW PWM were the maximum permitted value 252, the value at location TIMER ON would be 2520, while the value stored at location TIMER OFF would be 30. Using another example, if the linearized compensated value stored at the location NEW PWM were 100, at step 424 the routine LOOP would store the value 1000 at location TIMER ON and the value 1550 at location TIMER OFF.

After calculating the values for location TIMER ON and TIMER OFF, at step 442 routine LOOP provides the operator with an indication on the operator interface panel 250 of the nature of the shape of the bale being formed in the bale case. The provision of this indication is understood from routine BLSH which is described below with reference to FIG. 12. Thereafter, when execution returns to routine LOOP from routine BLSH, the routine completes its processing with respect to its compuation and utilization of the value at location NEW PWM. The routine LOOP will again be executed when execution jumps thereto in accordance with either step 368 or 380 of the routine ANALYSIS.

Figure 12:
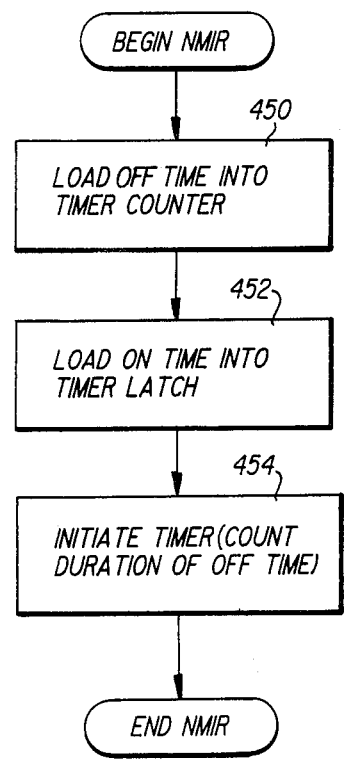
FIG. 12 is a diagrammatic schematic view showing processing steps associated with a routine NMIR executed by signal processing means.

The computation of the values for locations TIMER ON and TIMER OFF as conducted by routine LOOP provides a foundation for the understanding of the utilization of these values by routine NIMR for the generation and pulse width modulation of the control signal applied to the servo valve 61. In this regard, processing steps associated with the routine NMIR are shown in FIG. 12. At step 450 routine LOOP causes the value at location TIMER OFF to be loaded into a first timer comprising the PIA 204. Likewise, at step 452 the routine NMIR causes the value at location TIMER ON to be loaded into a latch associated with the first timer comprising the PIA 204. The execution of routine NMIR is initiated by interrupts generated every 2.5 milliseconds.

After the loading of the TIMER OFF value into the first timer, the first timer is decremented upon reception of E clock signals. While decrementing from the value corresponding the value at location TIMER OFF, pin 17 of the PIA 204 has a FALSE signal applied thereto. When the first timer is timed out with respect to the value of location TIMER OFF, the value from location TIMER ON is immediately moved from the latch into the timer whereby the timer begins to decrement from the value TIMER ON. While decrementing from the value TIMER ON the output pin 17 of the PIA 204 has a TRUE signal applied thereto. As the timer again times out the routine NMIR is reexecuted upon the next nonmaskable interrupt with respect to the next period of the control signal.

ROUTINE BLSH

In connection with step 442 of routine LOOP it was mentioned above that the operator is provided with an indication of the shape of the bale being formed in the bale case 20. In this regard, the baler may not be precisely centered over a windrow, with the result that a non-uniform feed into the bale case can cause an uneven stress on the plunger assembly 22 and possibly an uneven density distribution through the bale. The uneven stress on the plunger assembly 22 is experienced at two spaced apart locations on assembly 22, such as the locations of the left load cell 131L and the right load cell 131R.

Execution of steps included in the routine BLSH (see FIG. 11) facilitate a diagnostic display on an operator interface panel 250 whereby the operator is apprised of the need to better center the baler over the windrow. As seen hereinafter, routine BLSH basically determines the average conrod load; computes 10%, 15%, and 25% deviation values with respect to the average conrod load; determines the magnitude of the load differential between the average conrod load and the load on the greater stressed conrod; compares the magnitude of the differential with the 10%, 15%, and 25% deviation values; and, turns on various display blocks on panel 250 in accordance with the comparison, thereby providing the operator with an indication of the direction in which the bale case 20 should be manuevered to rectify the uneven feed and an indication of the degree of the present feed imbalance.

Figure 11:
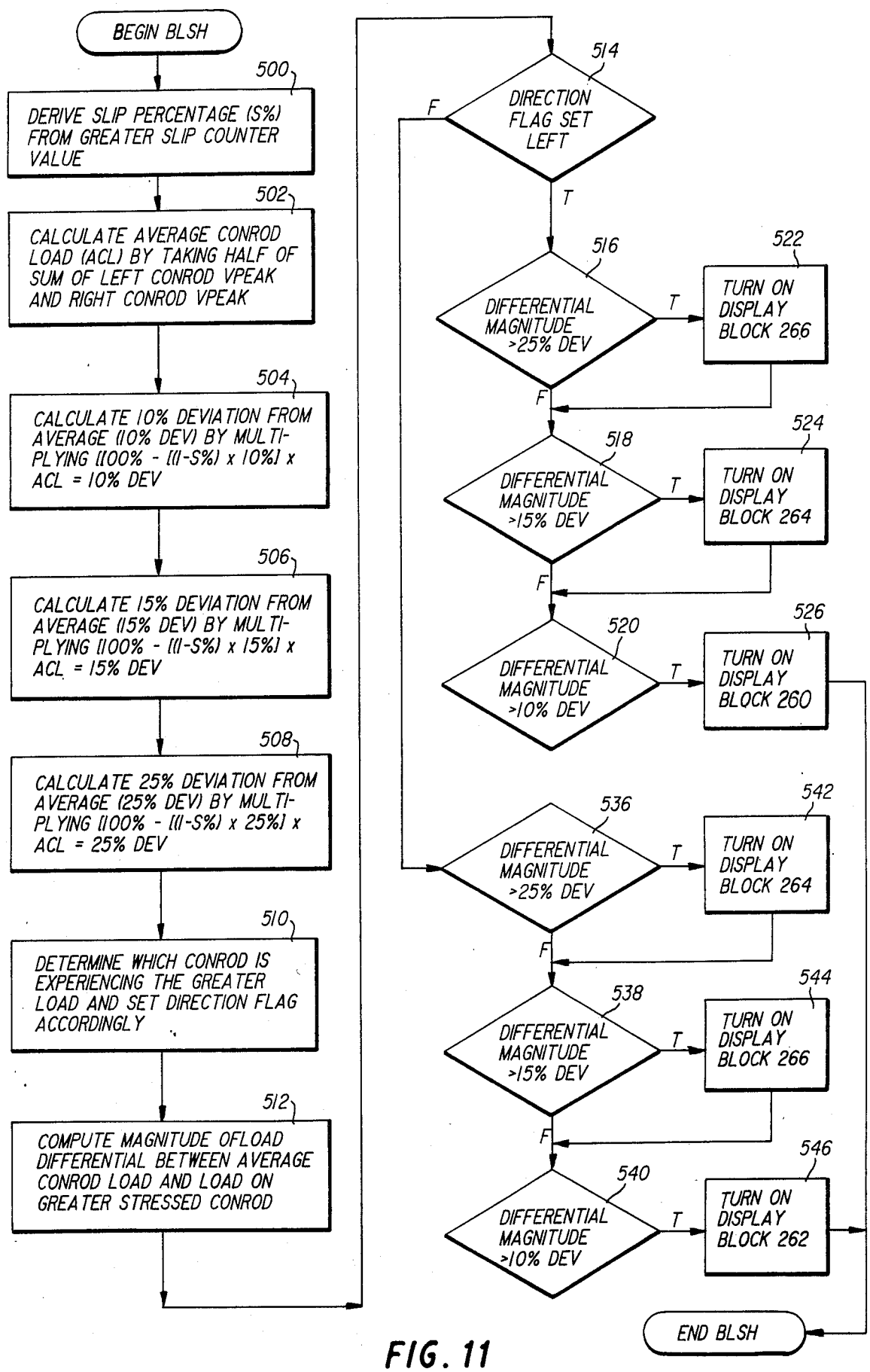
FIG. 11 is a diagrammatic schematic view showing processing steps associated with a routine BLSH executed by signal processing means.

With reference to the steps of FIG. 11, at step 500 routine BLSH derives a slip percentage (represented in FIG. 11 by S%) based on the value in counter LEFT SLIP or RIGHT SLIP, whichever is greater. At step 502 routine BLSH calculates the average conrod loading (ACL) by averaging the values in locations LEFT CONROD VPEAK and RIGHT CONROD VPEAK.

In steps 504, 506, and 508, respectively, routine BLSH determines 10% 15%, and 25% deviation values for eventual comparison purposes. The deviation values are determined using the expression $ACL \times [100\% - [(1-S\%) \times DEV\%]]$ where ACL is the average conrod loading (see step 502 above), S% is the slip percentage (see step 500 above) and DEV% is the deviation percentage (10% for step 504; 15% for step 106; 25% for step 508).

At step 510 routine BLSH determines which load cell is experiencing the greater stress by comparing the values in location LEFT CONROD PEAK and RIGHT CONROD PEAK. In accordance with the result the routine BLSH sets a flag DIRECTION in a manner to indicate whether the left load cell 131L or the right load cell 131R is experiencing the greater stress.

At step 512 routine BLSH computes the magnitude of the differential between the average conrod loading ACL and the load on the greater stressed load cell (using the appropriate "VPEAK" value). As seen hereinafter, this magnitude differential is compared with the various percent deviations to determine, in conjunction with the flag DIRECTION, which display blocks should be activated on operator interface panel 250.

At step 514 routine BLSH checks to determine whether the value of flag DIRECTION indicates that the left load cell 131L is the greater stressed. If so, in steps 515, 518, and 520 routine BLSH compares the magnitude of the differential computed in step 512 with the respective 25% DEV, 15% DEV, and 10% DEV values. If the magnitude of the differential exceeds 25% DEV, at step 522 routine BLSH causes display block 266 to be turned on. If the magnitude of the differential exceeds 15% DEV, at step 524 routine BLSH causes display block 264 to be turned on. If the magnitude of the differential exceeds 10% DEV, at step 526 routine BLSH causes display arrow 260 to be turned on.

Thus, if the baler is not centered over the windrow with the result that the left load cell 131L is experiencing the greater stress, routine BLSH serves to inform the operator by turning on arrow display 260 that the baler needs to be manuevered leftwardly. Moreover, the number of display blocks lit on the panel 250 provide the operator with an indication of the degree of stress inequality being experienced by the load cells. If arrow 260 alone is lit, a 10% stress inequality is represented. If arrow 260 and block 264 are lit, a 15% stress inequality is represented. If arrow 260, block 264, and block 266 are lit, a 25% stress inequality is represented.

In the event that it is determined at step 514 that the flag DIRECTION indicates that the right load cell 131R is the greater stressed, comparisons analagous to those made at steps 516, 518, and 520 are made at steps 536, 538, and 540 and appropriate ones of the display blocks 264, 266, and 262 are turned on accordingly (at steps 542, 544, and 546). Thus, if the right load cell 131R is experiencing a stress to the extent that the differential magnitude exceeds 25% DEV, display arrow 262 and display blocks 266 and 264 are turned on.

In turning on appropriate ones of the display blocks on the operator interface panel 250, the signal processor 200 communicates with the panel 250 through pins 9, 4, and 6 of PIA 206 as described above. It should be understood that types of indicators other than visual display indicators can be employed, and that any two spaced-apart locations on the plunger assembly 22 can be monitored in order to provide a similar indication of nonuniformity of stress or load. Further, although not shown in FIG. 11, it should be understood that the routine BLSH may require that a loading imbalance be determined for a predetermined number of executions before the display on the operator panel 250 is changed, thereby overriding very short fluctuations in the loading differential.

FIGS. 13A, 13B, 13C, AND 13D are graphs which illustrate various aspects of the operation steps described above. The horizontal axes of the graphs represent time; the veritcal axes are as respectively labeled.

FIG. 13B is a graph representing a windrow profile over a period of time (T) according to a hypothetical illustration. The graph of FIG. 13B has been plotted without reference to aspects of the baler described herein, i.e. the magnitude of crop material in the windrow has been measured by some other means for providing an understanding of the conditions reflected by the graph of FIG. 13A. It is also assumed that FIG. 13B generally reflects the magnitude of crop ingestation into the bale case 20, although it is understood that ingestation occurs in discrete charges.

According to FIG. 13B, the quantity of crop material in a first windrow gradually increases until approximately $T=2$, at which time the crop quantity starts to trail off. At time $T=3$ the baler begins to enter the headlands, with the result that essentially no crop ingestation occurs at time $T=4$. At about time $T=4.5$ the baler has turned around and begins to enter a second windrow, and fully enters the second windrow by time $T=5$. It is evident, of course, that the time axis of FIG. 13B has been drastically compressed in order to conveniently illustrate the operation of the baler and its signal processor 200 over a wide range of conditions. Despite the axis compression, the graphs of FIG. 13A-13D provide the reader with an understanding of the nature and effect of the steps described hereinbefore with reference to the signal processor 200 and its various executed routines.

The graph of FIG. 13A basically represents the load on or stress experienced by a load cell as the baler bales the crop material of the windrows having profiles depicted in FIG. 13B. The load or stress on the plunger assembly 22 is expressed in terms of measured voltage from the load cell, the peaks of the graph particularly corresponding to values stored at the corresponding times in location VPEAK. It is recalled that the routine ANALYSIS interprets voltage values associated with sensor interrupts from each load cell as a waveform, separate waveforms being analyzed for each load cell. For the purpose of describing the graph of FIG. 13A, it is assumed that for the time shown in FIG. 13A the waveforms associated with both load cells are essentially identical, it therefore being necessary to illustrate only one such waveform in FIG. 13A.

From FIG. 13A it is seen that peak voltages occur at points in time at which the plunger assembly 22 is experiencing the greatest stress in its application of compactive force to the material in the bale case. For purposes of discussion each peak-to-peak time span is described as a stroke. FIG. 13A shows 8 such strokes for a baler operating at a uniform PTO RPM.

From FIG. 13A it is also possible to determine an indication of the magnitude of crop material being ingested into the bale case 20. In this regard, in observing sensor output voltage signal waveforms it has been noted that, following a voltage peak, a voltage plateau is formed before the voltage tapers off significantly, and that the duration of this plateau corresponds substantially to the degree of bale slippage which occurs in the bale case following the application of compactive force by the plunger. Further, the degree of bale slippage has been observed as corresponding to the quantity of crop material being introduced into the bale case from the particular windrow over which the baler is travelling.

Using routine ANALYSIS signal processor 200 monitors the voltage waveform and essentially measures the duration of the plateau by incrementing the counters LEFT SLIP and RIGHT SLIP as long as the sensor voltage is within a predetermined neighborhood of the sensor voltage peak, particularly within 75% of the voltage sensor peak ("VPEAK") value. As indicated at step 424 of routine LOOP, the signal processor 200 uses the normalized value of the greater of the values in counters LEFT SLIP and RIGHT SLIP in determining whether sufficient crop material is being ingested to adjust the tension being applied to rails 54, 56 of the bale case 20. For FIG. 13A, the distance SC1 represents the relative value of the appropriate slip counter for stroke 1; the distance SC2 represents the relative value of the appropriate slip counter for stroke 2; and so forth.

From FIG. 13A it is observed that at time T=2 the voltage indicative of the stress on the monitored load cell has increased above the user-input set point value indicative of desired density. Accordingly, when executing routine LOOP the signal processor 200 subtracts (in accordance with step 430) an adjusted value from location DENSITY ERROR from the value at location PREVIOUS PWM to obtain a value NEW PWM. The value at location NEW PWM is checked, linearized, and compensated before routine LOOP prepares and stores values at locations TIMER OFF and TIMER ON in accordance with step 440. Upon the next non-maskable interrupt routine NMIR will use the new values at locations TIMER OFF and TIMER ON in accordance with the steps depicted in FIG. 12 to change the pulse width modulation of the control signal applied to servo valve 61. As seen in FIG. 13C, at about T=3 the decreased value in location NEW PWM results in a smaller value in location TIMER ON, which is reflected by shorter pulse widths for the control signal. Inasmuch as the servo valve 61 is a current-controlled pressure valve, the servo valve 61 has an inherent inductance whereby the pressure output from valve 61 is a time-averaged representation of the control signal. Thus, the shorter pulse widths of the control signal commenced at time T=3 serve to reduce the tension applied to the bale case rails, thereby slightly decreasing the density of the material being baled in the bale case 20 in order to urge density back to a value indicative of the desired density set point.

From FIGS. 13 it is seen that at essentially the same time the signal processor 200 causes the lessening of tension on the bale case rails 54, 56 (i.e. time T=3), the baler enters the headlands. Upon entering the headlands the stress experienced by the load cell considerably decreases and is shown as being below the desired density set point. Rather than immediately cause the tension on the bale case rails to be increased in response to the decreased stress on the load cell, the signal processor 200 checks (as at step 424 of routine LOOP) whether the normalized slip count indicates that an insufficient quantity of crop material is being ingested. By checking the appropriate slip counter at time T=4, the signal processor determines that the slip count (corresponding to distance SC4) is very small. Since the slip count represented by distance SC4 is below a predetermined value, signal processor 200 decides (at LOOP step 424) to clamp the tension being applied to the bale case rails 54, 56 at their previous level (by executing steps 428, 432, et seq. of routine LOOP). Thus, the control signal to servo valve 61 essentially remains constant until the signal processor 200 recognizes that the baler has again entered a windrow. Having maintained the tension applied to bale case rails 54, 56 at the previous level, the load cells are not overloaded when the baler enters the second windrow and considerable crop material is again ingested.

FIGS. 13 show that at time T=5 the baler enters the second windrow. At time T=6 the signal processor 200 checks the appropriate slip counter (represented by arrow SC6) and determines that sufficient crop material quantity is being ingested for further adjustment of bale case tension. Accordingly, at time T=6 the control signal to servo valve 61 is modulated whereby a greater tension is applied to the bale case rails 54, 56, whereby the density of the baled material approaches the desired density set point.

While the invention has been particularly shown and described with reference to the preferred embodiments thereof, it will be understood by those skilled in the art that various alterations in form and detail may be made therein without departing from the spirit and scope of the invention.

The embodiments of the invention in which an exclusive property or privilige is claimed are defined as follows:

1. Apparatus for controlling the density of bales of crop material discharged from an agricultural baling machine, said apparatus comprising:
   a bale case into which crop material is introduced;
   means for providing resistance to the movement of crop material in said bale case;
   means for changing the degree of resistance to said crop material movement in said bale case;
   a plunger assembly disposed for reciprocating movement in said bale case;
   means for reciprocably driving said plunger assembly in a manner whereby said plunger means applies a compactive force to crop material introduced into said bale case and thereby facilitates movement of said crop material through said bale case;
   means for sensing the stress experienced by said plunger assembly including stress experienced during the application of said compactive force applied by said plunger assembly and for producing a signal in accordance with said sensed stress;
   means for obtaining an indication of the quantity of crop material being introduced into said bale case; and,
   means for controlling said resistance changing means, said control means being adapted to utilize said indication of said crop introduction quantity and being responsive to said signal produced by said sensing means in its control of said resistance changing means.

2. The apparatus of claim 1, wherein said control means precludes said resistance changing means from increasing said resistance when said indication of said crop introduction quantity is below a predetermined value.

3. The apparatus of claim 1, wherein said means for obtaining an indication of the quantity of crop material being introduced into said bale case uses said signal produced by said sensing means to obtain said indication.

4. The apparatus of claim 3, wherein the magnitude of said signal varies from a first peak value to a second peak value in accordance with corresponding first and second applications of compactive force by said plunger assembly, and wherein the time period required for said signal to drop to a predetermined percentage of one of said peak values is used as an indication of the quantity of crop material being introduced into said bale case.

5. The apparatus of claim 4, wherein said machine operates in accordance with a PTO speed, and wherein for any current PTO speed said time period required for said signal to drop to a predetermined percentage of one of said peak values is normalized relative to a reference PTO value.

6. The apparatus of claim 5, wherein the time period between said peak values is used as an indication of current PTO speed.

7. The apparatus of claim 6, wherein said control means comprises signal processing means, said signal processing means being connected to said sensing means in a manner whereby said signal processing means periodically receives said signal produced by said sensing means, wherein said signal processing means comprises counter means, and wherein said signal processing means periodically determines said time periods with reference to said peak values in accordance with the receipt of said signal.

8. The apparatus of claim 1, wherein the magnitude of said signal varies between peak values in accordance with corresponding applications of compactive force by said plunger assembly, wherein said control means comprises signal processing means, said signal processing means being connected to said sensing means for periodic reception of magnitude values of said signal; and wherein said signal processing means comprises:
   a memory having a plurality of memory locations for storing therein successive received ones of said magnitude values;
   means for averaging the magnitude values stored in said memory locations to obtain a current average value; and,
   means for comparing said current average value to a previous average value in order to determine the occurrence of a peak value.

9. Apparatus for controlling the density of bales of crop material discharged from an agricultural baling machine, said apparatus comprising:
   a bale case into which crop material is introduced;
   a plunger assembly disposed for reciprocating movement in said bale case;
   means for reciprocably driving said plunger assembly in a manner whereby said plunger assembly applies a compactive force to crop material introduced into said bale case;
   sensing means comprising at least two sensors mounted in spaced apart relation with respect to said plunger assembly, said sensors being adapted to sense the stress experienced at two spaced-apart locations on said plunger assembly including stress experienced during the application of said compactive force applied by said plunger assembly;
   means connected to said sensing means for determining the differential in stress experienced at said spaced apart locations; and,
   means connected to said differential determination means for providing an indication facilitating the potential equalizing of stress on said spaced-apart plunger assembly locations.

10. The apparatus of claim 9, wherein said indication means provides an indication of a direction in which said machine should be manuvered in order to potentially equalize the stress on said spaced-apart plunger assembly locations.

11. The apparatus of claim 10, wherein said indication means provides an indication of the magnitude of the stress differential being experienced at said spaced-apart locations on said plunger assembly.

12. A method for controlling the density of bales of crop material discharged from a bale case of an agricultural baling machine, said method comprising the steps of:
   introducing crop material into said bale case;
   reciprocably driving a plunger assembly in a manner whereby said plunger means applies a compactive force to crop material introduced into said bale case and thereby facilitates movement of said crop material through said bale case;
   providing resistance to the movement of crop material introduced into said bale case;
   sensing the stress experienced by said plunger assembly including stress experienced during the application of said compactive force applied by said plunger assembly and for producing a signal in accordance with said sensed stress;
   obtaining an indication of the quantity of crop material being introduced into said bale case; and,
   controlling the degree of resistance to the movement of crop material introduced into said bale case in accordance with said indication of said crop introduction quantity and said signal.

13. The method of claim 12, wherein said step of controlling resistance includes the step of precluding an increase in said resistance when said indication of said crop introduction quantity is below a predetermined value.

14. The method of claim 12, wherein said step of obtaining an indication of the quantity of crop material being introduced into said bale case involves the step of using said signal produced by said sensing means to obtain said indication.

15. The method of claim 14, wherein the magnitude of said signal varies from a first peak value to a second peak value between corresponding first and second applications of compactive force by said plunger assembly, and wherein the time period required for said signal to drop to a predetermined percentage of one of said peak values is used as an indication of the quantity of crop material being introduced into said bale case.

16. The method of claim 15, wherein said machine operates in accordance with a PTO speed, and wherein for any current PTO speed said time period required for said signal to drop to a predetermined percentage of one of said peak values is normalized relative to a reference PTO value.

17. The method of claim 16, wherein the time period between said peak values is used as an indication of current PTO speed.

18. The method of claim 17, wherein said step of controlling said resistance comprises the steps of:
   receiving at signal processing means said signal produced by said sensing means; and,
   using said signal processing means to periodically determine said time periods with reference to said peak values in accordance with the receipt of said signal.

19. The method of claim 12, wherein the magnitude of said signal varies between peak values in accordance with corresponding applications of compactive force by said plunger assembly, wherein said step of controlling said resistance comprises:
   periodically receiving at signal processing means magnitude values of said signal;
   storing in a memory having a plurality of memory locations successive received ones of said magnitude values;
   averaging the magnitude values stored in said memory locations to obtain a current average value; and, comparing said current average value to a previous average value in order to determine the occurrence of a peak value.

20. A method for controlling the density of bales of crop material discharged from a bale case of an agricultural baling machine, said method comprising the steps of:
introducing crop material into said bale case;
reciprocably driving a plunger assembly in a manner whereby said plunger assembly applies a compactive force to crop material introduced into said bale case;
using sensing means comprising at least two sensors mounted in spaced apart relation with respect to said plunger assembly, said sensors being adapted to sense the stress experienced at two spaced-apart locations on said plunger assembly including stress experienced during the application of said compactive force applied by said plunger assembly;
determining the differential in stress experienced at said spaced apart locations; and,
providing an indication facilitating the potential equalizing of stress on said spaced-apart plunger assembly locations.

21. The apparatus of claim 20, wherein said step of providing an indication includes providing an indication of a direction in which said baling machine should be manuvered in order to potentially equalize the stress on said spaced-apart plunger assembly locations.

22. The method of claim 21, wherein the step of providing said indication includes providing an indication of the magnitude of the stress differential being experienced at said spaced-apart locations on said plunger assembly.

23. Apparatus for providing an indication of the quantity of crop material being fed into a bale case of an agricultural baling machine, said apparatus comprising:
a bale case into which crop material is introduced;
a plunger assembly disposed for reciprocating movement in said bale case;
means for reciprocably driving said plunger assembly in a manner whereby said plunger means applies a compactive force to crop material introduced into said bale case and thereby facilitates movement of said crop material through said bale case;
means for sensing the stress experienced by said plunger assembly including stress experienced during the application of said compactive force applied by said plunger assembly and for producing a signal in accordance with said sensed stress, the magnitude of said signal varying from peak value to peak value in accordance with corresponding applications of compactive force by said plunger assembly; and,
means for processing said signal in a manner whereby said signal peak values are detected and for using time period required for said signal to drop to a predetermined percentage of one of said peak values as an indication of the quantity of crop material being introduced into said bale case.

24. The apparatus of claim 23, wherein said machine operates in accordance with PTO speed, and wherein said machine operates in accordance with a PTO speed, and wherein for any current PTO speed said time period required for said signal to drop to a predetermined percentage of one of said peak values is normalized relative to a reference PTO value.

25. The apparatus of claim 24, wherein the time period between said peak values is used as an indication of current PTO speed.

26. The apparatus of claim 25, wherein said signal processing means is connected to said sensing means in a manner whereby said signal processing means periodically receives said signal produced by said sensing means, wherein said signal processing means comprises counter means, and wherein said signal processing means periodically determines said time periods with reference to said peak values in accordance with the receipt of said signal.

27. A method of providing an indication of the quantity of crop material being fed into a bale case of an agricultural baling machine, said method comprising the steps of:
introducing crop material into a bale case;
reciprocably driving a plunger assembly in a manner whereby said plunger means applies a compactive force to crop material introduced into said bale case and thereby facilitates movement of said crop material through said bale case;
sensing the stress experienced by said plunger assembly including stress experienced during the application of said compactive force applied by said plunger assembly and for producing a signal in accordance with said sensed stress, the magnitude of said signal varying from peak value to peak value in accordance with corresponding applications of compactive force by said plunger assembly; and,
processing said signal in a manner whereby said signal peak values are detected and whereby a time period required for said signal to drop to a predetermined percentage of one of said peak values is used as an indication of the quantity of crop material being introduced into said bale case.

28. The method of claim 27, wherein said machine operates in accordance with a current PTO speed, and wherein said method further comprises the step of:
normalizing said time period required for said signal to drop to a predetermined percentage of one of said peak values to a reference PTO speed.

29. The method of claim 28, further comprising the step of:
using a time period between said peak values as an indication of current PTO speed.

* * * * *

UNITED STATES PATENT AND TRADEMARK OFFICE
CERTIFICATE OF CORRECTION

PATENT NO. : 4,624,180
DATED : November 25, 1986
INVENTOR(S) : Richard P. Strosser It is certified that error appears in the above-identified patent and that said Letters Patent is hereby corrected as shown below:

The sheet of drawings comprising Figs. 3A, 3B, 3C, and 4 should be inserted as part of Letters Patent as shown on the attached sheet.

Signed and Sealed this

Twenty-sixth Day of September, 1989

*Attest:*

DONALD J. QUIGG

*Attesting Officer*     *Commissioner of Patents and Trademarks*